(12) United States Patent
Carrigan

(10) Patent No.: US 7,541,526 B1
(45) Date of Patent: *Jun. 2, 2009

(54) INBRED MAIZE LINE PHF1J

(75) Inventor: Lori Lisa Carrigan, Spicer, MN (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/938,901

(22) Filed: Nov. 13, 2007

Related U.S. Application Data

(63) Continuation of application No. 11/343,889, filed on Jan. 31, 2006, now Pat. No. 7,335,825.

(51) Int. Cl.
*A01H 5/00* (2006.01)
*A01H 5/10* (2006.01)
*A01H 1/00* (2006.01)
*C12N 5/04* (2006.01)

(52) U.S. Cl. ............... 800/320.1; 800/275; 800/300.1; 800/302; 435/412

(58) Field of Classification Search ................ None
See application file for complete search history.

(56) References Cited

U.S. PATENT DOCUMENTS

| 5,602,317 | A | 2/1997 | Luedtke |
| 5,792,915 | A | 8/1998 | Carrigan |
| 5,990,393 | A | 11/1999 | Chapman |
| 6,087,564 | A | 7/2000 | Cunnyngham |
| 6,806,408 | B1 | 10/2004 | Puskaric |
| 6,906,251 | B1 | 6/2005 | Morrow |
| 7,030,302 | B1 | 4/2006 | Piper |

OTHER PUBLICATIONS

Plant Variety Protection Cerfiticate No. 9700200 for Corn PH0AV, issued Oct. 27, 2000.
Plant Variety Protection Certificate No. 200100232 for Corn PH5TG, issued May 23, 2003.
Plant Variety Protection Certificate No. 9800378 for Corn PH1CN, issued May 8, 2001.

*Primary Examiner*—Elizabeth F McElwain
(74) *Attorney, Agent, or Firm*—McKee, Voorhees & Sease, P.L.C.

(57) ABSTRACT

A novel inbred maize line designated PHF1J and seed, plants and plant parts thereof. Methods for producing a maize plant that comprise crossing inbred maize line PHF1J with another maize plant. Methods for producing a maize plant containing in its genetic material one or more traits introgressed into PHF1J through backcross conversion and/or transformation, and to the maize seed, plant and plant part produced thereby. Hybrid maize seed, plant or plant part produced by crossing the inbred line PHF1J or a trait conversion of PHF1J with another maize line. Inbred maize lines derived from inbred maize line PHF1J, methods for producing other inbred maize lines derived from inbred maize line PHF1J and the inbred maize lines and their parts derived by the use of those methods.

6 Claims, No Drawings

INBRED MAIZE LINE PHF1J

CROSS-REFERENCE TO RELATED APPLICATIONS

This application is a continuation of U.S. patent application Ser. No. 11/343,889, now U.S. Pat. No. 7,335,825 filed on Jan. 31, 2006, the content of which is hereby incorporated by reference in its entirety.

FIELD OF THE INVENTION

This invention relates generally to the field of maize breeding, specifically relating to an inbred maize line designated PHF1J.

BACKGROUND OF THE INVENTION

The goal of plant breeding is to combine, in a single variety or hybrid, various desirable traits. For field crops, these traits may include resistance to diseases and insects, resistance to heat and drought, reducing the time to crop maturity, greater yield, and better agronomic quality. With mechanical harvesting of many crops, uniformity of plant characteristics such as germination, stand establishment, growth rate, maturity, plant height and ear height, is important. Traditional plant breeding is an important tool in developing new and improved commercial crops.

SUMMARY OF THE INVENTION

According to the invention, there is provided a novel inbred maize line, designated PHF1J and processes for making PHF1J. This invention relates to seed of inbred maize line PHF1J, to the plants of inbred maize line PHF1J, to plant parts of inbred maize line PHF1J, and to processes for making a maize plant that comprise crossing inbred maize line PHF1J with another maize plant. This invention also relates to processes for making a maize plant containing in its genetic material one or more traits introgressed into PHF1J through backcross conversion and/or transformation, and to the maize seed, plant and plant part produced by such introgression. This invention further relates to a hybrid maize seed, plant or plant part produced by crossing the inbred line PHF1J or an introgressed trait conversion of PHF1J with another maize line. This invention also relates to inbred maize lines derived from inbred maize line PHF1J to processes for making other inbred maize lines derived from inbred maize line PHF1J and to the inbred maize lines and their parts derived by the use of those processes.

DEFINITIONS

Certain definitions used in the specification are provided below. Also in the examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted. Below are the descriptors used in the data tables included herein.

ABTSTK=ARTIFICIAL BRITTLE STALK. A count of the number of "snapped" plants per plot following machine snapping. A snapped plant has its stalk completely snapped at a node between the base of the plant and the node above the ear. Expressed as percent of plants that did not snap.

ALLELE. Any of one or more alternative forms of a genetic sequence. Typically, in a diploid cell or organism, the two alleles of a given sequence typically occupy corresponding loci on a pair of homologous chromosomes.

ALTER. The utilization of up-regulation, down-regulation, or gene silencing.

ANTHESIS. The time of a flower's opening.

ANT ROT=ANTHRACNOSE STALK ROT (*Colletotrichum graminicola*). A 1 to 9 visual rating indicating the resistance to Anthracnose Stalk Rot. A higher score indicates a higher resistance. Data are collected only when sufficient selection pressure exists in the experiment measured.

BACKCROSSING. Process in which a breeder crosses a hybrid progeny line back to one of the parental genotypes one or more times.

BARPLT=BARREN PLANTS. The percent of plants per plot that were not barren (lack ears).

BORBMN=ARTIFICIAL BRITTLE STALK MEAN. The mean percent of plants not "snapped" in a plot following artificial selection pressure. A snapped plant has its stalk completely snapped at a node between the base of the plant and the node above the ear. Expressed as percent of plants that did not snap. A high number is good and indicates tolerance to brittle snapping.

BRENGMN=BRITTLE STALK ENERGY MEAN. The mean amount of energy per unit area needed to artificially brittle snap a corn stalk. A high number is good and indicates tolerance to brittle snapping.

BREEDING. The genetic manipulation of living organisms.

BREEDING CROSS. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed. For clarification, such new inbred varieties would be within a pedigree distance of one breeding cross of plants A and B. The process described above would be referred to as one breeding cycle.

BRTSTK=BRITTLE STALKS. This is a measure of the stalk breakage near the time of pollination, and is an indication of whether a hybrid or inbred would snap or break near the time of flowering under severe winds. Data are presented as percentage of plants that did not snap. Data are collected only when sufficient selection pressure exists in the experiment measured.

CELL. Cell as used herein includes a plant cell, whether isolated, in tissue culture or incorporated in a plant or plant part.

CLDTST=COLD TEST. The percent of plants that germinate under cold test conditions.

CLN=CORN LETHAL NECROSIS. Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance. Data are collected only when sufficient selection pressure exists in the experiment measured.

COMRST=COMMON RUST (*Puccinia sorghi*). A 1 to 9 visual rating indicating the resistance to Common Rust. A higher score indicates a higher resistance. Data are collected only when sufficient selection pressure exists in the experiment measured.

CROSS POLLINATION. A plant is cross pollinated if the pollen comes from a flower on a different plant from a different family or line. Cross pollination excludes sib and self pollination.

CROSS. As used herein, the term "cross" or "crossing" can refer to a simple X by Y cross, or the process of backcrossing, depending on the context.

D/D=DRYDOWN. This represents the relative rate at which a hybrid will reach acceptable harvest moisture compared to other hybrids on a 1 to 9 rating scale. A high score indicates a hybrid that dries relatively fast while a low score indicates a hybrid that dries slowly.

DIPERS=*DIPLODIA* EAR MOLD SCORES (*Diplodia maydis* and *Diplodia macrospora*). A 1 to 9 visual rating indicating the resistance to *Diplodia* Ear Mold. A higher score indicates a higher resistance. Data are collected only when sufficient selection pressure exists in the experiment measured.

DIPLOID PLANT PART. Refers to a plant part or cell that has the same diploid genotype as PHF1J.

DIPROT=*DIPLODIA* STALK ROT SCORE. Score of stalk rot severity due to *Diplodia* (*Diplodia maydis*). Expressed as a 1 to 9 score with 9 being highly resistant. Data are collected only when sufficient selection pressure exists in the experiment measured.

DRPEAR=DROPPED EARS. A measure of the number of dropped ears per plot and represents the percentage of plants that did not drop ears prior to harvest. Data are collected only when sufficient selection pressure exists in the experiment measured.

D/T=DROUGHT TOLERANCE. This represents a 1 to 9 rating for drought tolerance, and is based on data obtained under stress conditions. A high score indicates good drought tolerance and a low score indicates poor drought tolerance. Data are collected only when sufficient selection pressure exists in the experiment measured.

EARHT=EAR HEIGHT. The ear height is a measure from the ground to the highest placed developed ear node attachment and is measured in centimeters.

EARMLD=GENERAL EAR MOLD. Visual rating (1 to 9 score) where a 1 is very susceptible and a 9 is very resistant. This is based on overall rating for ear mold of mature ears without determining the specific mold organism, and may not be predictive for a specific ear mold. Data are collected only when sufficient selection pressure exists in the experiment measured.

EARSZ=EAR SIZE. A 1 to 9 visual rating of ear size. The higher the rating the larger the ear size.

EBTSTK=EARLY BRITTLE STALK. A count of the number of "snapped" plants per plot following severe winds when the corn plant is experiencing very rapid vegetative growth in the V5-V8 stage. Expressed as percent of plants that did not snap. Data are collected only when sufficient selection pressure exists in the experiment measured.

ECB1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance. Data are collected only when sufficient selection pressure exists in the experiment measured.

ECB21T=EUROPEAN CORN BORER SECOND GENERATION INCHES OF TUNNELING (*Ostrinia nubilalis*). Average inches of tunneling per plant in the stalk. Data are collected only when sufficient selection pressure exists in the experiment measured.

ECB2SC=EUROPEAN CORN BORER SECOND GENERATION (*Ostrinia nubilalis*). A 1 to 9 visual rating indicating post flowering degree of stalk breakage and other evidence of feeding by second generation European Corn Borer. A higher score indicates a higher resistance. Data are collected only when sufficient selection pressure exists in the experiment measured.

ECBDPE=EUROPEAN CORN BORER DROPPED EARS (*Ostrinia nubilalis*). Dropped ears due to European Corn Borer. Percentage of plants that did not drop ears under second generation European Corn Borer infestation. Data are collected only when sufficient selection pressure exists in the experiment measured.

ECBLSI=EUROPEAN CORN BORER LATE SEASON INTACT (*Ostrinia nubilalis*). A 1 to 9 visual rating indicating late season intactness of the corn plant given damage (stalk breakage above and below the top ear) caused primarily by $2^{nd}$ and/or $3^{rd}$ generation ECB larval feeding before harvest. A higher score is good and indicates more intact plants. Data are collected only when sufficient selection pressure exists in the experiment measured.

EGRWTH=EARLY GROWTH. This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute higher score. Data are collected only when sufficient selection pressure exists in the experiment measured.

ELITE INBRED. An inbred that contributed desirable qualities when used to produce commercial hybrids. An elite inbred may also be used in further breeding for the purpose of developing further improved varieties.

ERTLDG=EARLY ROOT LODGING. The percentage of plants that do not root lodge prior to or around anthesis; plants that lean from the vertical axis at an approximately 30 degree angle or greater would be counted as root lodged. Data are collected only when sufficient selection pressure exists in the experiment measured.

ERTLPN=EARLY ROOT LODGING. An estimate of the percentage of plants that do not root lodge prior to or around anthesis; plants that lean from the vertical axis at an approximately 30 degree angle or greater would be considered as root lodged. Data are collected only when sufficient selection pressure exists in the experiment measured.

ERTLSC=EARLY ROOT LODGING SCORE. Score for severity of plants that lean from a vertical axis at an approximate 30 degree angle or greater which typically results from strong winds prior to or around flowering recorded within 2 weeks of a wind event. Expressed as a 1 to 9 score with 9 being no lodging. Data are collected only when sufficient selection pressure exists in the experiment measured.

ESTCNT=EARLY STAND COUNT. This is a measure of the stand establishment in the spring and represents the number of plants that emerge on per plot basis for the inbred or hybrid.

EYESPT=EYE SPOT (*Kabatiella zeae* or *Aureobasidium zeae*). A 1 to 9 visual rating indicating the resistance to Eye Spot. A higher score indicates a higher resistance. Data are collected only when sufficient selection pressure exists in the experiment measured.

FUSERS=FUSARIUM EAR ROT SCORE (*Fusarium moniliforme* or *Fusarium subglutinans*). A 1 to 9 visual rating indicating the resistance to *Fusarium* Ear Rot. A higher score indicates a higher resistance. Data are collected only when sufficient selection pressure exists in the experiment measured.

GDU=GROWING DEGREE UNITS. Using the Barger Heat Unit Theory, which assumes that maize growth occurs in the temperature range 50 degrees F. –86 degrees F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86 degrees F. and the lowest minimum temperature used is 50 degrees F. For each inbred or hybrid it takes a certain number of GDUs to reach various stages of plant development.

GDUSLK=GDU TO SILK. The number of growing degree units required for an inbred line or hybrid to have approximately 50 percent of the plants with silk emergence from time of planting. Growing degree units are calculated by the Barger Method as given in GDU SHD definition.

GENE SILENCING. The interruption or suppression of the expression of a gene at the level of transcription or translation.

GENOTYPE. Refers to the genetic constitution of a cell or organism.

GIBERS=GIBBERELLA EAR ROT (PINK MOLD) (*Gibberella zeae*). A 1 to 9 visual rating indicating the resistance to *Gibberella* Ear Rot. A higher score indicates a higher resistance. Data are collected only when sufficient selection pressure exists in the experiment measured.

GIBROT=GIBBERELLA STALK ROT SCORE. Score of stalk rot severity due to *Gibberella* (*Gibberella zeae*). Expressed as a 1 to 9 score with 9 being highly resistant. Data are collected only when sufficient selection pressure exists in the experiment measured.

GLFSPT=GRAY LEAF SPOT (*Cercospora zeae-maydis*). A 1 to 9 visual rating indicating the resistance to Gray Leaf Spot. A higher score indicates a higher resistance. Data are collected only when sufficient selection pressure exists in the experiment measured.

GOSWLT=GOSS' WILT (*Corynebacterium nebraskense*). A 1 to 9 visual rating indicating the resistance to Goss' Wilt. A higher score indicates a higher resistance. Data are collected only when sufficient selection pressure exists in the experiment measured.

GRNAPP=GRAIN APPEARANCE. This is a 1 to 9 rating for the general appearance of the shelled grain as it is harvested based on such factors as the color of harvested grain, any mold on the grain, and any cracked grain. High scores indicate good grain visual quality.

HAPLOID PLANT PART. Refers to a plant part or cell that has the same haploid genotype as PHF1J.

HCBLT=*HELMINTHOSPORIUM CARBONUM* LEAF BLIGHT (*Helminthosporium carbonum*). A 1 to 9 visual rating indicating the resistance to *Helminthosporium* infection. A higher score indicates a higher resistance. Data are collected only when sufficient selection pressure exists in the experiment measured.

HD SMT=HEAD SMUT (*Sphacelotheca reiliana*). This score indicates the percentage of plants not infected. Data are collected only when sufficient selection pressure exists in the experiment measured.

HSKCVR=HUSK COVER. A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

INBRED. A line developed through inbreeding or doubled haploidy that preferably comprises homozygous alleles at about 95% or more of its loci.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. Gross income advantage of variety #1 over variety #2.

INTROGRESSION. The process of transferring genetic material from one genotype to another.

KSZDCD=KERNEL SIZE DISCARD. The percent of discard seed; calculated as the sum of discarded tip kernels and extra large kernels.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

LOCUS. A defined segment of DNA.

L/POP=YIELD AT LOW DENSITY. Yield ability at relatively low plant densities on a 1 to 9 relative system with a higher number indicating the hybrid responds well to low plant densities for yield relative to other hybrids. A 1, 5, and 9 would represent very poor, average, and very good yield response, respectively, to low plant density.

LRTLDG=LATE ROOT LODGING. The percentage of plants that do not root lodge after anthesis through harvest; plants that lean from the vertical axis at an approximately 30 degree angle or greater would be counted as root lodged. Data are collected only when sufficient selection pressure exists in the experiment measured.

LRTLPN=LATE ROOT LODGING. An estimate of the percentage of plants that do not root lodge after anthesis through harvest; plants that lean from the vertical axis at an approximately 30 degree angle or greater would be considered as root lodged. Data are collected only when sufficient selection pressure exists in the experiment measured.

LRTLSC=LATE ROOT LODGING SCORE. Score for severity of plants that lean from a vertical axis at an approximate 30 degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging. Data are collected only when sufficient selection pressure exists in the experiment measured.

MDMCPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance. Data are collected only when sufficient selection pressure exists in the experiment measured.

MST=HARVEST MOISTURE. The moisture is the actual percentage moisture of the grain at harvest.

MSTADV=MOISTURE ADVANTAGE. The moisture advantage of variety #1 over variety #2 as calculated by: MOISTURE of variety #2−MOISTURE of variety #1=MOISTURE ADVANTAGE of variety #1.

NEI DISTANCE. A quantitative measure of percent similarity between two lines. Nei's distance between lines A and B can be defined as 1−(2*number alleles in common/(number alleles in A+number alleles in B). For example, if lines A and B are the same for 95 out of 100 alleles, the Nei distance would be 0.05. If lines A and B are the same for 98 out of 100 alleles, the Nei distance would be 0.02. Free software for calculating Nei distance is available on the internet at multiple locations such as, for example, at: evolution.genetics.washington.edu/phylip.html. See Nei, Proc Natl Acad Sci, 76:5269-5273 (1979) which is incorporated by reference for this purpose.

NLFBLT=NORTHERN LEAF BLIGHT (*Helminthosporium turcicum* or *Exserohilum turcicum*). A 1 to 9 visual rating indicating the resistance to Northern Leaf Blight. A higher score indicates a higher resistance. Data are collected only when sufficient selection pressure exists in the experiment measured.

OILT=GRAIN OIL. Absolute value of oil content of the kernel as predicted by Near-Infrared Transmittance and expressed as a percent of dry matter.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two inbred lines. Each inbred plant will have the same allele (and therefore be homozygous) at almost all of their loci. Percent identity is determined by comparing a statistically significant number of the homozygous alleles of two inbred lines. For example, a percent identity of 90% between inbred PHF1J and other inbred line means that the two inbred lines have the same allele at 90% of their loci.

PERCENT SIMILARITY. Percent similarity as used herein refers to the comparison of the homozygous alleles of an inbred line with another plant. The homozygous alleles of PHF1J are compared with the alleles of a non-inbred plant, such as a hybrid, and if the allele of the inbred matches at least one of the alleles from the hybrid then they are scored as similar. Percent similarity is determined by comparing a statistically significant number of loci and recording the number of loci with similar alleles as a percentage. For example, a percent similarity of 90% between inbred PHF1J and a hybrid maize plant means that the inbred line matches at least one of the hybrid alleles at 90% of the loci. In the case of a hybrid produced from PHF1J as the male or female parent, such hybrid will comprise two sets of alleles, one set of which will comprise the same alleles as the homozygous alleles of inbred line PHF1J.

PLANT. As used herein, the term "plant" includes reference to an immature or mature whole plant, including a plant that has been detasseled or from which seed or grain has been removed. Seed or embryo that will produce the plant is also considered to be the plant.

PLANT PARTS. As used herein, the term "plant parts" includes leaves, stems, roots, seed, grain, embryo, pollen, ovules, flowers, ears, cobs, husks, stalks, root tips, anthers, pericarp, silk, tissue, cells and the like.

PLTHT=PLANT HEIGHT. This is a measure of the height of the plant from the ground to the tip of the tassel in centimeters.

POLSC=POLLEN SCORE. A 1 to 9 visual rating indicating the amount of pollen shed. The higher the score the more pollen shed.

POLWT=POLLEN WEIGHT. This is calculated by dry weight of tassels collected as shedding commences minus dry weight from similar tassels harvested after shedding is complete.

POP K/A=PLANT POPULATIONS. Measured as 1000s per acre.

POP ADV=PLANT POPULATION ADVANTAGE. The plant population advantage of variety #1 over variety #2 as calculated by PLANT POPULATION of variety #2−PLANT POPULATION of variety #1=PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRMSHD=A relative measure of the growing degree units (GDU) required to reach 50% pollen shed. Relative values are predicted values from the linear regression of observed GDU's on relative maturity of commercial checks.

PROT=GRAIN PROTEIN. Absolute value of protein content of the kernel as predicted by Near-Infrared Transmittance and expressed as a percent of dry matter.

RESISTANCE. Synonymous with tolerance. The ability of a plant to withstand exposure to an insect, disease, herbicide or other condition. A resistant plant variety will have a level of resistance higher than a comparable wild-type variety.

RTLDG=ROOT LODGING. Root lodging is the percentage of plants that do not root lodge; plants that lean from the vertical axis at an approximately 30 degree angle or greater would be counted as root lodged. Data are collected only when sufficient selection pressure exists in the experiment measured.

RTLADV=ROOT LODGING ADVANTAGE. The root lodging advantage of variety #1 over variety #2. Data are collected only when sufficient selection pressure exists in the experiment measured.

SCTGRN=SCATTER GRAIN. A 1 to 9 visual rating indicating the amount of scatter grain (lack of pollination or kernel abortion) on the ear. The higher the score the less scatter grain.

SDGVGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SELF POLLINATION. A plant is self-pollinated if pollen from one flower is transferred to the same or another flower of the same plant.

SIB POLLINATION. A plant is sib-pollinated when individuals within the same family or line are used for pollination.

SINGLE LOCUS CONVERSION TRAIT. A trait that can be introgressed into a corn line through introgression and/or transformation of a single locus. Examples of such single locus traits include mutant genes, transgenes and native traits finely mapped to a single locus. One or more single locus conversion traits may be introduced into a single corn line.

SLFBLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance. Data are collected only when sufficient selection pressure exists in the experiment measured.

SOURST=SOUTHERN RUST (*Puccinia polysora*). A 1 to 9 visual rating indicating the resistance to Southern Rust. A higher score indicates a higher resistance. Data are collected only when sufficient selection pressure exists in the experiment measured.

STAGRN=STAY GREEN. Stay green is the measure of plant health near the time of black layer formation (physiological maturity). A high score indicates better late-season plant health.

STDADV=STALK STANDING ADVANTAGE. The advantage of variety #1 over variety #2 for the trait STK CNT.

STKCNT=NUMBER OF PLANTS. This is the final stand or number of plants per plot.

STKLDG=STALK LODGING REGULAR. This is the percentage of plants that did not stalk lodge (stalk breakage) at regular harvest (when grain moisture is between about 20 and 30%) as measured by either natural lodging or pushing the stalks and determining the percentage of plants that break below the ear. Data are collected only when sufficient selection pressure exists in the experiment measured.

STKLDS=STALK LODGING SCORE. A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging. Data are collected only when sufficient selection pressure exists in the experiment measured.

STLLPN=LATE STALK LODGING. This is the percent of plants that did not stalk lodge (stalk breakage or crimping) at or around late season harvest (when grain moisture is below 20%) as measured by either natural lodging or pushing the stalks and determining the percentage of plants that break or crimp below the ear. Data are collected only when sufficient selection pressure exists in the experiment measured.

STLPCN=STALK LODGING REGULAR. This is an estimate of the percentage of plants that did not stalk lodge (stalk breakage) at regular harvest (when grain moisture is between about 20 and 30%) as measured by either natural lodging or pushing the stalks and determining the percentage of plants that break below the ear. Data are collected only when sufficient selection pressure exists in the experiment measured.

STRT=GRAIN STARCH. Absolute value of starch content of the kernel as predicted by Near-Infrared Transmittance and expressed as a percent of dry matter.

STWWLT=Stewart's Wilt (*Erwinia stewartii*). A 1 to 9 visual rating indicating the resistance to Stewart's Wilt. A higher score indicates a higher resistance. Data are collected only when sufficient selection pressure exists in the experiment measured.

TASBLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting. Data are collected only when sufficient selection pressure exists in the experiment measured.

TASSZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEXEAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data are given as a percentage of tillers: number of tillers per plot divided by number of plants per plot.

TSTWT=TEST WEIGHT (UNADJUSTED). The measure of the weight of the grain in pounds for a given volume (bushel).

TSWADV=TEST WEIGHT ADVANTAGE. The test weight advantage of variety #1 over variety #2.

WIN M %=PERCENT MOISTURE WINS.

WIN Y %=PERCENT YIELD WINS.

YIELD BU/A=YIELD (BUSHELS/ACRE). Yield of the grain at harvest by weight or volume (bushels) per unit area (acre) adjusted to 15% moisture.

YLDADV=YIELD ADVANTAGE. The yield advantage of variety #1 over variety #2 as calculated by: YIELD of variety #1−YIELD variety #2=YIELD ADVANTAGE of variety #1.

YLDSC=YIELD SCORE. A 1 to 9 visual rating was used to give a relative rating for yield based on plot ear piles. The higher the rating the greater visual yield appearance.

Definitions for Area of Adaptability

When referring to area of adaptability, such term is used to describe the location with the environmental conditions that would be well suited for this maize line. Area of adaptability is based on a number of factors, for example: days to maturity, insect resistance, disease resistance, and drought resistance. Area of adaptability does not indicate that the maize line will grow in every location within the area of adaptability or that it will not grow outside the area.

Central Corn Belt: Iowa, Illinois, Indiana

Drylands: non-irrigated areas of North Dakota, South Dakota, Nebraska, Kansas, Colorado, and Oklahoma Eastern U.S.: Ohio, Pennsylvania, Delaware, Maryland, Virginia, and West Virginia North central U.S.: Minnesota and Wisconsin Northeast: Michigan, New York, Vermont, and Ontario and Quebec Canada Northwest U.S.: North Dakota, South Dakota, Wyoming, Washington, Oregon, Montana, Utah, and Idaho South central U.S.: Missouri, Tennessee, Kentucky, Arkansas Southeast U.S.: North Carolina, South Carolina, Georgia, Florida, Alabama, Mississippi, and Louisiana Southwest U.S.: Texas, Oklahoma, New Mexico, Arizona Western U.S.: Nebraska, Kansas, Colorado, and California Maritime Europe Northern France, Germany, Belgium, Netherlands and Austria

DETAILED DESCRIPTION OF THE INVENTION AND FURTHER EMBODIMENTS

All tables discussed in the Detailed Description of the Invention and Further Embodiments section can found at the end of the section.

Morphological and Physiological Characteristics of PHF1J

Inbred maize line PHF1J is a yellow-orange flint-dent maize inbred that may be used as either a male or female in the production of the first generation F1 maize hybrid although PHF1J may be best suited for use as a male. Inbred maize line PHF1J is best adapted to the Northwest, Northeast, Northcentral, West, and Dryland regions of the United States, as well as Canada and Continental Europe. Inbred maize line PHF1J can be used to produce hybrids with approximately 90 to 95 maturity based on the Comparative Relative Maturity Rating System. Inbred maize line PHF1J demonstrates excellent seedling emergence, high Common Smut resistance, strong Anthracnose resistance as well as Ear Mold resistance. In hybrid combinations, PHF1J demonstrates high grain yield, strong drydown, excellent seedling emergence, above average late season plant health and stalk strength.

The inbred has shown uniformity and stability within the limits of environmental influence for all the traits as described in the Variety Description Information (Table 1, found at the end of the section). The inbred has been self-pollinated and ear-rowed a sufficient number of generations with careful attention paid to uniformity of plant type to ensure the homozygosity and phenotypic stability necessary for use in commercial hybrid seed production. The line has been increased both by hand and in isolated fields with continued observation for uniformity. No variant traits have been observed or are expected in PHF1J.

Inbred maize line PHF1J, being substantially homozygous, can be reproduced by planting seeds of the line, growing the resulting maize plants under self-pollinating or sib-pollinating conditions with adequate isolation, and harvesting the resulting seed using techniques familiar to the agricultural arts.

Genotypic Characteristics of PHF1J

In addition to phenotypic observations, a plant can also be identified by its genotype. The genotype of a plant can be characterized through a genetic marker profile, which can identify plants of the same variety or a related variety, or be used to determine or validate a pedigree. The SSR profile of Inbred PHF1J can be found in Table 2 at the end of this section. As a result of inbreeding, PHF1J is substantially homozygous. This homozygosity has been characterized at the loci shown in the marker profile provided herein. An F1 hybrid made with PHF1J would comprise the marker profile of PHF1J shown herein. This is because an F1 hybrid is the sum of its inbred parents, e.g., if one inbred parent is homozygous for allele x at a particular locus, and the other inbred parent is homozygous for allele y at that locus, the F1 hybrid will be x.y (heterozygous) at that locus. The profile can therefore be used to identify hybrids comprising PHF1J as a parent, since such hybrids will comprise two sets of alleles, one set of which will be from PHF1J. The determination of the male set of alleles and the female set of alleles may be made by profiling the hybrid and the pericarp of the hybrid seed, which is composed of maternal parent cells. One way to obtain the paternal parent profile is to subtract the pericarp profile from the hybrid profile.

Subsequent generations of progeny produced by selection and breeding are expected to be of genotype x (homozygous), y (homozygous), or x.y (heterozygous) for these locus positions. When the F1 plant is used to produce an inbred, the resulting inbred should be either x or y for that allele. In that regard, a unique allele or combination of alleles unique to that inbred can be used to identify progeny plants that retain those unique alleles or combinations of alleles.

Therefore, in accordance with the above, an embodiment of this invention is a PHF1J progeny maize plant or plant part that is a first generation (F1) hybrid maize plant comprising two sets of alleles, wherein one set of the alleles is the same as PHF1J at all of the SSR loci listed in Table 2. A maize cell wherein one set of the alleles is the same as PHF1J at all of the SSR loci listed in Table 2 is also an embodiment of the invention. This maize cell may be a part of a hybrid seed, plant or plant part produced by crossing PHF1J with another inbred maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don et al., "Assessing Probability of Ancestry Using Simple Sequence Repeat Profiles: Applications to Maize Hybrids and Inbreds", Genetics, 2002, 161:813-824, and Berry, Don et al., "Assessing Probability of Ancestry Using Simple Sequence Repeat Profiles: Applications to Maize Inbred Lines and Soybean Varieties", Genetics, 2003, 165: 331-342.

Particular markers used for these purposes are not limited to the set of markers disclosed herein, but may include any type of marker and marker profile which provides a means of distinguishing varieties. In addition to being used for identification of Inbred maize line PHF1J, a hybrid produced through the use of PHF1J, and the identification or verification of pedigree for progeny plants produced through the use of PHF1J, the genetic marker profile is also useful in further breeding and in developing an introgressed trait conversion of PHF1J.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing lines it is preferable if all SSR profiles are performed in the same lab. The SSR analyses reported herein were conducted in-house at Pioneer Hi-Bred. An SSR service is available to the public on a contractual basis by DNA Landmarks in Saint-Jean-sur-Richelieu, Quebec, Canada.

Primers used for the SSRs reported herein are publicly available and may be found in the Maize GDB on the World Wide Web at maizegdb.org (sponsored by the USDA Agricultural Research Service), in Sharopova et al. (Plant Mol. Biol. 48(5-6):463-481), Lee et al. (Plant Mol. Biol. 48(5-6); 453-461), or may be constructed from sequences if reported herein. Primers may be constructed from publicly available sequence information. Some marker information may also be available from DNA Landmarks.

Map information is provided by bin number as reported in the Maize GDB for the IBM 2 and/or IBM 2 Neighbors maps. The bin number digits to the left of decimal point represent the chromosome on which such marker is located, and the digits to the right of the decimal represent the location on such chromosome. A bin number.xx designation indicates that the bin location on that chromosome is not known. Map positions are also available on the Maize GDB for a variety of different mapping populations.

PHF1J and its plant parts can be identified through a molecular marker profile. An inbred corn plant cell having the SSR genetic marker profile shown in Table 2 is an embodiment of the invention. Such plant cell may be either diploid or haploid.

Also encompassed within the scope of the invention are plants and plant parts substantially benefiting from the use of PHF1J in their development, such as PHF1J comprising a introgressed trait through backcross conversion or transformation, and which may be identified by having an SSR molecular marker profile with a high percent identity to PHF1J, such as at least 80%, 81%, 82%, 83%, 84%, 85%, 86%, 87%, 88%, 89%, 90%, 91%, 92%, 93%, 94%, 95%, 96%, 97%, 98%, 99% or 99.5% identity. Likewise, percent similarity at these percentages may be used to identify hybrid and other non-inbred plants produced by the use of PHF1J.

An embodiment of this invention is an inbred PHF1J progeny maize plant or plant part comprising the same homozygous alleles as the plant or plant part of PHF1J for at least 90% of the SSR loci listed in Table 2. A plant cell comprising the same homozygous alleles as a plant cell of PHF1J for at least 90% of the SSR loci listed in Table 2 is also an embodiment of this invention. In these specific embodiments, 90% may also be replaced by any integer or partial integer percent of 80% or greater as listed above. One means of producing such a progeny plant, plant part or cell is through the backcrossing and/or transformation methods described herein.

Similarly, an embodiment of this invention is a PHF1J progeny maize plant or plant part comprising at least one allele per locus that is the same allele as the plant or plant part of PHF1J for at least 90% of the SSR loci listed in Table 2. This progeny plant may be a hybrid. A progeny or hybrid plant cell wherein at least one allele per locus that is the same allele as the plant cell PHF1J for at least 90% of the SSR loci listed in Table 2 is also a specific embodiment of this invention. In these specific embodiments, 90% may also be replaced by any integer percent listed above. One means of producing such a progeny or hybrid plant, plant part or cell is through the backcrossing and/or transformation methods described herein.

In addition, the SSR profile of PHF1J also can be used to identify essentially derived varieties and other progeny lines developed from the use of PHF1J, as well as cells and other plant parts thereof. Progeny plants and plant parts produced using PHF1J may be identified by having a molecular marker profile of at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PHF1J, as measured by either percent identity or percent similarity.

Comparing PHF1J to Other Inbreds

A breeder uses various methods to help determine which plants should be selected from segregating populations and ultimately which inbred lines will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987). Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide, insect or disease resistance. Similarly, an introgressed trait conversion of PHF1J for resistance, such as herbicide resistance, should not be compared to PHF1J in the presence of the herbicide when comparing non-resistance related traits such as plant height and yield.

In Table 3, data from traits and characteristics of inbred maize line PHF1J per se are given and compared to other maize inbred lines and hybrids. The following are the results of these comparisons. The results in Table 3 show inbred PHF1J has significantly different traits compared to other maize inbred lines.

The results in Table 3A compare inbred PHF1J to inbred PH5TG. The results show inbred PHF1J has significantly different yield, moisture, early stand count, pollen weight, plant height, and percent of barren plants compared to PH5TG.

The results in Table 3B compare inbred PHF1J to inbred PHAA0. The results show inbred PHF1J differs significantly over multiple traits including yield, moisture, early stand count, tassel size and percent of barren plants when compared to inbred PHAA0.

The results in Table 3C compare inbred PHF1J to inbred PH0AV. The results show inbred PHF1J differs significantly from PH0AV in a number of traits including early growth, number of growing degree units required for 50% of the plants to be shedding pollen, and tassel size.

Development of Maize Hybrids using PHF1J

A single cross maize hybrid results from the cross of two inbred lines, each of which has a genotype that complements the genotype of the other. The hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

PHF1J may be used to produce hybrid maize. One such embodiment is the method of crossing inbred maize line PHF1J with another maize plant, such as a different maize inbred line, to form a first generation F1 hybrid seed. The first generation F1 hybrid seed, plant and plant part produced by this method is an embodiment of the invention. The first generation F1 seed, plant and plant part will comprise an essentially complete set of the alleles of inbred line PHF1J. One of ordinary skill in the art can utilize either breeder books or molecular methods to identify a particular F1 hybrid plant produced using inbred line PHF1J. Further, one of ordinary skill in the art may also produce F1 hybrids with transgenic, male sterile and/or backcross conversions of inbred line PHF1J The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, such as PHF1J, which, although different from each other, breed true and are highly uniform; and (3) crossing the selected inbred lines with different inbred lines to produce the hybrids. During the inbreeding process in maize, the vigor of the lines decreases, and so one would not be likely to use PHF1J directly to produce grain. However, vigor is restored when PHF1J is crossed to a different inbred line to produce a commercial F1 hybrid. An important consequence of the homozygosity and homogeneity of the inbred line is that the hybrid between a defined pair of inbreds may be reproduced indefinitely as long as the homogeneity of the inbred parents is maintained.

PHF1J may be used to produce a single cross hybrid, a double cross hybrid, or a three-way hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. In each case, pericarp tissue from the female parent will be a part of and protect the hybrid seed.

Combining Ability of PHF1J

Combining ability of a line, as well as the performance of the line per se, is a factor in the selection of improved maize inbreds. Combining ability refers to a line's contribution as a parent when crossed with other lines to form hybrids. The hybrids formed for the purpose of selecting superior lines may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the lines.

General combining ability provides an overall score for the inbred over a large number of test crosses. Specific combining ability provides information on hybrid combinations formed by PHF1J and a specific inbred parent. A line such as PHF1J which exhibits good general combining ability may be used in a large number of hybrid combinations.

A general combining ability report for inbred PHF1J is provided in Table 4. This data represents the overall mean value for these traits over hundreds of test crosses. Table 4 demonstrates that inbred PHF1J shows good general combining ability for hybrid production.

Hybrid Comparisons

These hybrid comparisons represent specific hybrid crosses with PHF1J and a comparison of these specific hybrids with other hybrids with favorable characteristics. These comparisons illustrate the good specific combining ability of PHF1J.

The results in Table 5 compare a specific hybrid for which inbred PHF1J is a parent with other hybrids. The results show that inbred PHF1J shows good specific combining ability.

The data in Table 6 show that numerous species of the genus of F1 hybrids created with PHF1J have been reduced to practice. Phenotypic data are presented for these hybrids and are based on replicated field trials. Of course, many more species of this genus may be created by one of ordinary skill in the art without undue experimentation by crossing PHF1J with a multitude of publicly available inbred lines. For example, see J. T. Gerdes et al., *Compilation of North American Maize Breeding Germplasm*, pp. 1-87 (Crop Science Society of America, 1993) which is incorporated by reference for this purpose.

Introgression of a New Locus or Trait into PHF1J

PHF1J represents a new base genetic line into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of PHF1J

A backcross conversion of PHF1J occurs when DNA sequences are introduced through backcrossing (Hallauer et al. in Corn and Corn Improvement, Sprague and Dudley, Third Ed. 1998), with PHF1J utilized as the recurrent parent. Both naturally occurring and transgenic DNA sequences may be introduced through backcrossing techniques. A backcross conversion may produce a plant with a trait or locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding, In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, waxy starch, sterility (nuclear and cytoplasmic), fertility restoration, grain color (white), nutritional enhancements, drought resistance, enhanced nitrogen utilization efficiency, altered nitrogen responsiveness, altered fatty acid profile, increased digestibility, low phytate, industrial enhancements, disease resistance (bacterial, fungal or viral), insect resistance, herbicide resistance and yield enhancements. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into PHF1J is at least 1, 2, 3, 4, or 5 and/or no more than 6, 5, 4, 3, or 2. A single loci may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci. Further, SSI and FRT technologies known to those of skill in the art in the art may result in multiple gene introgressions at a single locus.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. While occasionally additional polynucleotide sequences or genes may be transferred along with the backcross conversion, the backcross conversion line "fits into the same hybrid combination as the recurrent parent inbred line and contributes the effect of the additional gene added through the backcross." Poehlman et al. (1995, page 334). It has been proposed that in general there should be at least four backcrosses when it is important that the recovered lines be essentially identical to the recurrent parent except for the characteristic being transferred (Fehr 1987, Principles of Cultivar Development). However, as noted above, the number of backcrosses necessary can be reduced with the use of molecular markers. Other factors, such as a genetically similar donor parent, may also reduce the number of backcrosses necessary.

One process for adding or modifying a trait or locus in maize inbred line PHF1J comprises crossing PHF1J plants grown from PHF1J seed with plants of another maize line that comprise the desired trait or locus, selecting F1 progeny plants that comprise the desired trait or locus to produce selected F1 progeny plants, crossing the selected progeny plants with the PHF1J plants to produce backcross progeny plants, selecting for backcross progeny plants that have the desired trait or locus and the morphological characteristics of maize inbred line PHF1J to produce selected backcross progeny plants; and backcrossing to PHF1J three or more times in succession to produce selected fourth or higher backcross progeny plants that comprise said trait or locus. The modified PHF1J may be further characterized as having the physiological and morphological characteristics of maize inbred line PHF1J listed in Table 1 as determined at the 5% significance level when grown in the same environmental conditions and/or may be characterized by percent similarity or identity to PHF1J as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration.

In addition, the above process and other similar processes described herein may be used to produce F1 hybrid maize seed by adding a step at the end of the process that comprises crossing PHF1J with the introgressed trait or locus with a different maize plant and harvesting the resultant F1 hybrid maize seed.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

PHF1J can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile inbred designated PHF1J may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's, and the male sterility trait is routinely backcrossed into inbred lines. See Wych, p. 585-586,1998.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 publication no. 329, 308 and PCT application PCT/CA90/00037 published as WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be one of the inbred lines used to produce the hybrid. Though the possibility of inbred PHF1J being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, 1-8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20(1) p. 29-42.

An embodiment of this invention is a process for producing seed of PHF1J comprising planting a collection of seed comprising seed of a hybrid, one of whose parents is inbred PHF1J said collection also comprising seed of said inbred, growing plants from said collection of seed, identifying inbred parent plants, selecting said inbred parent plant; and controlling pollination to preserve the homozygosity of said inbred parent plant.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, a transformed variant of PHF1J may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transformed versions of the claimed inbred maize line PHF1J as well as hybrid combinations thereof.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular maize plant using transformation techniques, could be moved into the genome of another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953, which are herein incorporated by reference. In addition, transformability of a line can be increased by introgressing the trait of high transformability from another line known to have high transformability, such as Hi-II. See U.S. Patent Application Publication US2004/0016030 (2004).

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, Methods in Plant Molecular Biology and Biotechnology 269-284 (CRC Press, Boca Raton,1993).

Wang et al. discuss "Large Scale Identification, Mapping and Genotyping of Single-Nucleotide Polymorphisms in the Human Genome", Science, 280:1077-1082, 1998, and similar capabilities are available for the corn genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of maize the expression of genes can be altered to enhance disease resistance, insect resistance, herbicide resistance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) Plant Cell 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*); McDowell & Woffenden, (2003) Trends Biotechnol. 21 (4): 178-83 and Toyoda et al., (2002) Transgenic Res. 11 (6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Btdelta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, U.S. application Ser. Nos. 10/389,432,10/692,367, and U.S. Pat. No. 6,563,020.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO03000863 and U.S. application Ser. No. 10/178,213.

(T) Genes conferring resistance to nematodes. See WO 03/033651 and Urwin et. al., Planta 204:472-479 (1998), Williamson (1999) Curr Opin Plant Bio. 2(4):327-31.

(U) Genes such as rcg1 conferring resistance to Anthracnose stalk rot, which is caused by the fungus *Colletotrichum graminiola*. See M. Jung et al., Generation-means analysis and quantitative trait locus mapping of Anthracnose Stalk Rot genes in Maize, *Theor. Appl. Genet.* (1994) 89:413-418 which is incorporated by reference for this purpose, as well as U.S. Patent Application 60/675,664, which is also incorporated by reference for this purpose.

2. Transgenes that Confer Resistance to a Herbicide, For Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.*

7:1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Application Serial Nos. US01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bargenes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include: a gene encoding a chimeric protein of rat cytochrome P4507A1 and yeast NADPH-cytochrome P450 oxidoreductase (Shiota et al. (1994) Plant Physiol. 106(1):17-23), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such As:

(A) Altered fatty acids, for example, by (1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AG P, Dek1, Superal1, mi 1 ps, various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO02/057439, WO03/011015 and Rivera-Madrid, R. et. al. Proc. Natl. Acad. Sci. 92:5620-5624 (1995).

(B) Altered phosphorus content, for example, by the (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO99/05298, U.S. Pat. No. 6,197,561, U.S. Pat. No. 6,291,224, U.S. Pat. No. 6,391,348, WO2002/059324, US2003/0079247, Wo98/45448, WO99/55882, WO01/04147.

(C) Altered carbohydrates effected, for example, by altering a gene for an enzyme that affects the branching pattern of starch or a gene altering thioredoxin such as NTR and/or TRX (see U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., *J. Bacteriol.* 170: 810 (1988) (nucleotide sequence of

*Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FR1), WO97/29123, U.S. Pat. No. 6,794,560, U.S. Pat. No. 6,307,126 (GAI), WO99/09174 (D8 and Rht), and WO2004076638 and WO2004031349 (transcription factors).

Using PHF1J to Develop Other Maize Inbreds

Inbred maize lines such as PHF1J are typically developed for use in the production of hybrid maize lines. However, inbred lines such as PHF1J also provide a source of breeding material that may be used to develop new maize inbred lines. Plant breeding techniques known in the art and used in a maize plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits but genotypic analysis may also be used.

Using PHF1J in a Breeding Program

This invention is directed to methods for producing a maize plant by crossing a first parent maize plant with a second parent maize plant wherein either the first or second parent maize plant is an inbred maize plant of the line PHF1J. The other parent may be any other maize plant, such as another inbred line or a plant that is part of a synthetic or natural population. Any such methods using the inbred maize line PHF1J are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can also be found in one of several reference books (e.g., Allard, *Principles of Plant Breeding*, 1960; Simmonds, *Principles of Crop Improvement*, 1979; Fehr, "Breeding Methods for Cultivar Development", *Production and Uses*, $2^{nd}$ ed., Wilcox editor, 1987 the disclosure of which is incorporated herein by reference).

Pedigree Breeding

Pedigree breeding starts with the crossing of two genotypes, such as PHF1J and one other elite inbred line having one or more desirable characteristics that is lacking or which complements PHF1J. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify PHF1J and a hybrid that is made using the modified PHF1J. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line PHF1J, comprising the steps of crossing a plant of maize inbred line PHF1J with a donor plant comprising a mutant gene or transgene conferring a desired trait, selecting an F1 progeny plant comprising the mutant gene or transgene conferring the desired trait, and backcrossing the selected F1 progeny plant to a plant of maize inbred line PHF1J. This method may further comprise the step of obtaining a molecular marker profile of maize inbred line PHF1J and using the molecular marker profile to select for a progeny plant with the desired trait and the molecular marker profile of PHF1J. In the same manner, this method may be used to produce an F1 hybrid seed by adding a final step of crossing the desired trait conversion of maize inbred line PHF1J with a different maize plant to make F1 hybrid maize seed comprising a mutant gene or transgene conferring the desired trait.

Recurrent Selection and Mass Selection

Recurrent selection is a method used in a plant breeding program to improve a population of plants. PHF1J is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation Breeding

Mutation breeding is one of many methods that could be used to introduce new traits into PHF1J. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993 Macmillan Publishing Company, the disclosure of which is incorporated herein by reference. In addition, mutations created in other lines may be used to produce a backcross conversion of PHF1J that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing PHF1J.

Isozyme Electrophoresis and RFLPs as discussed in Lee, M., "Inbred Lines of Maize and Their Molecular Markers," *The Maize Handbook*, (Springer-Verlag, New York, Inc. 1994, at 423-432), have been widely used to determine genetic composition. Isozyme Electrophoresis has a relatively low number of available markers and a low number of allelic variants among maize inbreds. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (*Zea mays* L.): comparisons with data from RFLPs and pedigree", *Theoretical and Applied Genetics* (1997) vol. 95 at 163-173 and by Pejic et al., "Comparative analysis of genetic similarity among maize inbreds detected by RFLPs, RAPDs, SSRs, and AFLPs," *Theoretical and Applied Genetics* (1998) at 1248-1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining their unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of inbreds in the breeding program. For example, an F1 hybrid for which PHF1J is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, *Am. Nat.* 93:381-382; Sharkar and Coe, 1966, *Genetics* 54:453-464) RWS (see world wide web site www.uni-hohenheim.de/%7Eipspwww/350b/ indexe.html#Project3), KEMS (Deimling, Roeber, and Geiger, 1997, *Vortr. Pflanzenzuchtg*38:203-224), or KMS and ZMS (Chalyk, Bylich & Chebotar, 1994, *MNL* 68:47; Chalyk & Chebotar, 2000, *Plant Breeding* 119:363-364), and indeterminate gametophyte (ig) mutation (Kermicle 1969 *Science* 166:1422-1424). The disclosures of which are incorporated herein by reference.

Methods for obtaining haploid plants are also disclosed in Kobayashi, M. et al., *Journ. of Heredity* 71(1):9-14, 1980, Pollacsek, M., Agronomie (Paris) 12(3):247-251,1992; Cho-Un-Haing et al., *Journ. of Plant Biol.*, 1996, 39(3):185-188; Verdoodt, L., et al., Feb. 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, *Maize Genet Coop. News-* letter 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P. et al., 1988, *Theor. Appl. Genet.* 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, *Indian J Genet Plant Breed* 38:452-457; Chalyk S. T., 1994, Euphytica 79:13-18; Chase, S. S., 1952, *Agron. J.* 44:263-267; Coe, E. H., 1959, *Am. Nat.* 93:381-382; Coe, E. H., and Sarkar, K. R., 1964 *J. Hered.* 55:231-233; Greenblatt, I. M. and Bock, M., 1967, *J. Hered.* 58:9-13; Kato, A., 1990, *Maize Genet. Coop. Newsletter* 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951 and U.S. patent application Ser. No. 10/121,200, the disclosures of which are incorporated herein by reference.

Thus, an embodiment of this invention is a process for making a substantially homozygous PHF1J progeny plant by producing or obtaining a seed from the cross of PHF1J and another maize plant and applying double haploid methods to the F1 seed or F1 plant or to any successive filial generation. Such methods decrease the number of generations required to produce an inbred with similar genetics or characteristics to PHF1J. See Bernardo, R. and Kahler, A. L., Theor. Appl. Genet. 102:986-992, 2001.

In particular, a process of making seed retaining the molecular marker profile of maize inbred line PHF1J is contemplated, such process comprising obtaining or producing F1 hybrid seed for which maize inbred line PHF1J is a parent, inducing doubled haploids to create progeny without the occurrence of meiotic segregation, obtaining the molecular marker profile of maize inbred line PHF1J, and selecting progeny that retain the molecular marker profile of PHF1J.

Use of PHF1J in Tissue Culture

This invention is also directed to the use of PHF1J in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widholm, Planta (1985) 165: 322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in *Plant Cell Reports* (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. 2002/0062506A1 and European Patent Application, publication EP0160,390, each of which are incorporated herein by reference for this purpose. Maize tissue culture procedures are also described in Green and Rhodes, "Plant Regeneration in Tissue Culture of Maize," *Maize for Biological Research* (Plant Molecular Biology Association, Charlottesville, Virginia 1982, at 367-372) and in Duncan, et al., "The Production of Callus Capable of Plant Regeneration from Immature Embryos of Numerous *Zea Mays* Genotypes," 165 Planta 322-332 (1985). Thus, another aspect of this invention is to provide cells which upon growth and differentiation produce maize plants having the genotype and/or physiological and morphological characteristics of inbred line PHF1J.

Progeny Plants

All plants produced by the use of the methods described herein and that retain the unique genetic or trait combinations of PHF1J are within the scope of the invention. Progeny of the breeding methods described herein may be characterized in any number of ways, such as by traits retained in the progeny, pedigree and/or molecular markers. Combinations of these methods of characterization may be used.

Breeder's of ordinary skill in the art have developed the concept of an "essentially derived variety", which is defined in 7 U.S.C. § 2104(a)(3) of the Plant Variety Protection Act and is hereby incorporated by reference. Varieties and plants that are essentially derived from PHF1J are within the scope of the invention.

Pedigree is a method used by breeders of ordinary skill in the art to describe the varieties. Varieties that are more closely related by pedigree are likely to share common genotypes and combinations of phenotypic characteristics. All breeders of ordinary skill in the art maintain pedigree records of their breeding programs. These pedigree records contain a detailed description of the breeding process, including a listing of all parental lines used in the breeding process and information on how such line was used. One embodiment of this invention is progeny plants and parts thereof with at least one ancestor that is PHF1J, and more specifically, where the pedigree of the progeny includes 1, 2, 3, 4, and/or 5 or less breeding crosses to a maize plant other than PHF1J or a plant that has PHF1J as a parent or other progenitor. A breeder of ordinary skill in the art would know if PHF1J were used in the development of a progeny line, and would also know how many crosses to a line other than PHF1J or line with PHF1J as a parent or other progenitor were made in the development of any progeny line.

Molecular markers also provide a means by which those of ordinary skill in the art characterize the similarity or differences of two lines. Using the breeding methods described herein, one can develop individual plants, plant cells, and populations of plants that retain at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PHF1J, as measured by either percent identity or percent similarity. On average 50% of the starting germplasm would be expected to be passed to the progeny line after one cross to another line, 25% after another cross to a different line, and so on. With backcrossing, the expected contribution of PHF1J after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

Traits are also used by those of ordinary skill in the art to characterize progeny. Traits are commonly evaluated at a significance level, such as a 1%, 5% or 10% significance level, when measured in plants grown in the same environmental conditions. For example, a backcross conversion of PHF1J may be characterized as having the same morphological and physiological traits as PHF1J. The traits used for comparison may be those traits shown in Table 1, Table 3, Table 4 or Table 5.

A breeder will commonly work to combine a specific trait of an undeveloped variety of the species, such as a high level of resistance to a particular disease, with one or more of the elite agronomic characteristics (yield, maturity, plant size, lodging resistance, etc.) needed for use as a commercial variety. This combination, once developed, provides a valuable source of new germplasm for further breeding. For example, it may take 10-15 years and significant effort to produce such a combination, yet progeny may be developed that retain this combination in as little as 2-5 years and with much less effort.

SPECIFIC EMBODIMENTS

Specific methods and products produced using inbred line PHF1J in plant breeding are discussed in the following sections. The methods outlined are described in detail by way of illustration and example for purposes of clarity and understanding. However, it will be obvious that certain changes and modifications may be practiced within the scope of the invention.

One method for producing a line derived from inbred line PHF1J is as follows. One of ordinary skill in the art would produce or obtain a seed from the cross between inbred line PHF1J and another variety of maize, such as an elite inbred variety. The F1 seed derived from this cross would be grown to form a homogeneous population. The F1 seed would contain essentially all of the alleles from variety PHF1J and essentially all of the alleles from the other maize variety. The F1 nuclear genome would be made-up of 50% variety PHF1J and 50% of the other elite variety. The F1 seed would be grown and allowed to self, thereby forming F2 seed. On average the F2 seed would have derived 50% of its alleles from variety PHF1J and 50% from the other maize variety, but many individual plants from the population would have a greater percentage of their alleles derived from PHF1J (Wang J. and R. Bernardo, 2000, Crop Sci. 40:659-665 and Bernardo, R. and A. L. Kahler, 2001, Theor. Appl. Genet. 102: 986-992). The molecular markers of PHF1J could be used to select and retain those lines with high similarity to PHF1J. The F2 seed would be grown and selection of plants would be made based on visual observation, markers and/or measurement of traits. The traits used for selection may be any PHF1J trait described in this specification, including the inbred per se maize PHF1J traits described herein under the detailed description of inbred PHF1J. Such traits may also be the good general or specific combining ability of PHF1J, including its ability to produce hybrids with the approximate maturity and/or hybrid combination traits described herein under the detailed description of inbred PHF1J. The PHF1J progeny plants that exhibit one or more of the desired PHF1J traits, such as those listed herein, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable PHF1J traits listed herein. The process of growing and selection would be repeated any number of times until a PHF1J progeny inbred plant is obtained. The PHF1J progeny inbred plant would contain desirable traits derived from inbred plant PHF1J, some of which may not have been expressed by the other maize variety to which inbred line PHF1J was crossed and some of which may have been expressed by both maize varieties but now would be at a level equal to or greater than the level expressed in inbred variety PHF1J. However, in each case the resulting progeny line would benefit from the efforts of the inventor(s), and would not have existed but for the inventor(s) work in creating PHF1J. The PHF1J progeny inbred plants would have, on average, 50% of their nuclear genes derived from inbred line PHF1J, but many individual plants from the population would have a greater percentage of their alleles derived from PHF1J. This breeding cycle, of crossing and selfing, and optional selection, may be repeated to produce another population of PHF1J progeny maize plants with, on average, 25% of their nuclear genes derived from inbred line PHF1J, but, again, many individual plants from the population would have a greater percentage of their alleles derived from PHF1J. This process can be repeated for a third, fourth, fifth, sixth, seventh or more breeding cycles. Another embodiment of the invention is a PHF1J progeny plant that has received the desirable PHF1J traits listed herein through the use of PHF1J, which traits were not exhibited by other plants used in the breeding process.

Therefore, an embodiment of this invention is a PHF1J progeny maize plant, wherein at least one ancestor of said PHF1J progeny maize plant is the maize plant or plant part of PHF1J, and wherein the pedigree of said PHF1J progeny maize plant is within two breeding crosses of PHF1J or a plant that has PHF1J as a parent. The progeny plants, parts and plant cells produced from PHF1J may be further characterized as having a percent marker similarity or identity with PHF1J as described herein.

The previous example can be modified in numerous ways, for instance selection may or may not occur at every selfing generation, selection may occur before or after the actual self-pollination process occurs, or individual selections may be made by harvesting individual ears, plants, rows or plots at any point during the breeding process described. Double haploid breeding methods may be used at any step in the process. Instead of selfing out of the hybrid produced from the inbred, one could first cross the hybrid to either a parent line or a different inbred, and then self out of that cross.

The population of plants produced at each and any cycle of breeding is also an embodiment of the invention, and on average each such population would predictably consist of plants containing approximately 50% of its genes from inbred line PHF1J in the first breeding cycle, 25% of its genes from inbred line PHF1J in the second breeding cycle, 12.5% of its genes from inbred line PHF1J in the third breeding cycle, 6.25% in the fourth breeding cycle, 3.125% in the fifth breeding cycle, and so on. However, in each case the use of PHF1J provides a substantial benefit. The linkage groups of PHF1J would be retained in the progeny lines, and since current estimates of the maize genome size is about 50,000-80,000 genes (Xiaowu, Gai et al., Nucleic Acids Research, 2000, Vol. 28, No. 1, 94-96), in addition to non-coding DNA that impacts gene expression, it provides a significant advantage to use PHF1J as starting material to produce a line that retains desired genetics or traits of PHF1J.

Therefore, an embodiment of the invention is a process for making a population of PHF1J progeny inbred maize plants comprising obtaining or producing a first generation progeny maize seed comprising the plant of PHF1J as a parent, growing said first generation progeny maize seed to produce first generation maize plants and obtaining self or sib pollinated seed from said first generation maize plants, and growing the self or sib pollinated seed to obtain a population of PHF1J progeny inbred maize plants.

The population of PHF1J progeny inbred maize plants produced by this method are also embodiments of the invention, and such population as a whole will retain the expected genetic contribution of PHF1J. An inbred line selected from the population of PHF1J progeny inbred maize plants produced by this method is an embodiment, and such line may be further characterized by its molecular marker identity or similarity to PHF1J.

In this manner, the invention also encompasses a process for making a PHF1J inbred progeny maize plant comprising the steps of obtaining or producing a first generation progeny maize seed wherein a parent of said first generation progeny maize seed is a PHF1J plant, growing said first generation progeny maize seed to produce a first generation maize plant and obtaining self or sib pollinated seed from said first generation maize plant, and producing successive filial generations to obtain a PHF1J inbred progeny maize plant. Also an embodiment of this invention is the first breeding cycle inbred PHF1J maize plant produced by this method.

Crosses to Other Species

The utility of inbred maize line PHF1J also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with PHF1J may be the various varieties of grain sorghum, *Sorghum bicolor* (L.) Moench.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line PHF1J, the plant produced from the inbred seed, the hybrid maize plant produced from the crossing of the inbred, hybrid seed, and various parts of the hybrid maize plant and transgenic versions of the foregoing, can be utilized for human food, livestock feed, and as a raw material in industry.

REFERENCES

Aukerman, M. J. et al. (2003) "Regulation of Flowering Time and Floral Organ Identity by a MicroRNA and Its APETALA2-like Target Genes" *The Plant Cell* 15:2730-2741

Berry et al., Berry, Don et al., "Assessing Probability of Ancestry Using Simple Sequence Repeat Profiles: Applications to Maize Hybrids and Inbreds", Genetics 161:813-824 (2002)

Berry et al., "Assessing Probability of Ancestry Using Simple Sequence Repeat Profiles: Applications to Maize Inbred Lines and Soybean Varieties" Genetics 165:331-342 (2003)

Boppenmaier, et al., "Comparisons Among Strains of Inbreds for RFLPs", Maize Genetics Cooperative Newsletter, 65:1991, p. 90

Conger, B. V., et al. (1987) "Somatic Embryogenesis From Cultured Leaf Segments of *Zea Mays*", *Plant Cell Reports*, 6:345-347

Duncan, D. R., et al. (1985) "The Production of Callus Capable of Plant Regeneration From Immature Embryos of Numerous *Zea Mays* Genotypes", *Planta*, 165:322-332

Edallo, et al. (1981) "Chromosomal Variation and Frequency of Spontaneous Mutation Associated with in Vitro Culture and Plant Regeneration in Maize", *Maydica*, XXVI:39-56

Fehr, Walt, Principles of Cultivar Development, pp. 261-286 (1987)

Green, et al. (1975) "Plant Regeneration From Tissue Cultures of Maize", *Crop Science*, Vol. 15, pp. 417-421

Green, C. E., et al. (1982) "Plant Regeneration in Tissue Cultures of Maize" *Maize for Biological Research*, pp. 367-372

Hallauer, A. R. et al. (1988) "Corn Breeding" *Corn and Corn Improvement*, No. 18, pp. 463-481

Lee, Michael (1994) "Inbred Lines of Maize and Their Molecular Markers", *The Maize Handbook*, Ch. 65:423-432

Meghji, M. R., et al. (1984) "Inbreeding Depression, Inbred & Hybrid Grain Yields, and Other Traits of Maize Genotypes Representing Three Eras", *Crop Science*, Vol. 24, pp. 545-549

Openshaw, S. J., et al. (1994) "Marker-assisted selection in backcross breeding". pp. 41-43. In Proceedings of the Symposium Analysis of Molecular Marker Data. 5-7 Aug. 1994. Corvallis, Oreg., American Society for Horticultural Science/Crop Science Society of America Phillips, et al. (1988) "Cell/Tissue Culture and In Vitro Manipulation", *Corn & Corn Improvement*, $3^{rd}$ Ed., ASA Publication, No. 18, pp. 345-387

Poehlman et al (1995) *Breeding Field Crop*, 4th Ed., Iowa State University Press, Ames, Iowa., pp. 132-155 and 321-344

Rao, K. V., et al., (1986) "Somatic Embryogenesis in Glume Callus Cultures", *Maize Genetics Cooperative Newsletter*, No. 60, pp. 64-65

Sass, John F. (1977) "Morphology", *Corn & Corn Improvement*, ASA Publication, Madison, Wis. pp. 89-109

Smith, J. S. C., et al., "The Identification of Female Selfs in Hybrid Maize: A Comparison Using Electrophoresis and Morphology", Seed Science and Technology 14, 1-8

Songstad, D. D. et al. (1988) "Effect of ACC(1-aminocyclopropane-1-carboyclic acid), Silver Nitrate & Norbonadiene on Plant Regeneration From Maize Callus Cultures", *Plant Cell Reports,* 7:262-265

Tomes, et al. (1985) "The Effect of Parental Genotype on Initiation of Embryogenic Callus From Elite Maize (*Zea Mays* L.) Germplasm", *Theor. Appl. Genet.,* Vol. 70, p. 505-509

Troyer, et al. (1985) "Selection for Early Flowering in Corn: 10 Late Synthetics", *Crop Science,* Vol. 25, pp. 695-697

Umbeck, et al. (1983) "Reversion of Male-Sterile T-Cytoplasm Maize to Male Fertility in Tissue Culture", *Crop Science,* Vol. 23, pp. 584-588

Wan et al., "Efficient Production of Doubled Haploid Plants Through Colchicine Treatment of Anther-Derived Maize Callus", Theoretical and Applied Genetics, 77:889-892, 1989

Wright, Harold (1980) "Commercial Hybrid Seed Production", *Hybridization of Crop Plants,* Ch. 8:161-176

Wych, Robert D. (1988) "Production of Hybrid Seed", *Corn and Corn Improvement,* Ch. 9, pp. 565-607

DEPOSITS

Applicant has made a deposit of at least 2500 seeds of Inbred Maize Line PHF1J with the American Type Culture Collection (ATCC), Manassas, Va. 20110 USA, ATCC Deposit No. PTA-7773. The seeds deposited with the ATCC on Aug. 9, 2006 were taken from the deposit maintained by Pioneer Hi-Bred International, Inc., 7250 NW 62$^{nd}$ Avenue, Johnson, Iowa 50131-1000 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C. F. R. § 1.808. This deposit of the Inbred Maize Line PHF1J will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C. F. R. §§1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.). U.S. Plant Variety Protection of Inbred Maize Line PHF1J has been applied for. Unauthorized seed multiplication is prohibited.

TABLE 1

VARIETY DESCRIPTION INFORMATION
PHF1J

| | | | AVG | STDEV | N |
|---|---|---|---|---|---|
| 1. TYPE: (Describe intermediate types in comments section) | | | | | |
| 1 = Sweet, 2 = Dent, 3 = Flint, 4 = Flour, 5 = Pop and | | | 3 | | |
| 6 = Ornamental. | | | | | |
| Comments: Flint-Dent | | | | | |
| 2. MATURITY: DAYS HEAT UNITS | Days | H. Units | | | |
| Emergence to 50% of plants in silk | 58 | 1,228 | | | |
| Emergence to 50% of plants in pollen shed | 56 | 1,188 | | | |
| 10% to 90% pollen shed | 1 | 28 | | | |
| 50% Silk to harvest at 25% moisture | | | | | |
| 3. PLANT: | | | | | |
| Plant Height (to tassel tip) (cm) | | | 189.2 | 14.21 | 10 |
| Ear Height (to base of top ear node) (cm) | | | 66.2 | 15.98 | 10 |
| Length of Top Ear Internode (cm) | | | 14.5 | 0.71 | 10 |
| Average Number of Tillers per Plant | | | 0.0 | 0.01 | 2 |
| Average Number of Ears per Stalk | | | 0.8 | 0.27 | 2 |
| Anthocyanin of Brace Roots: 1 = Absent, 2 = Faint, | | | 4 | | |
| 3 = Moderate, 4 = Dark | | | | | |
| 4. LEAF: | | | | | |
| Width of Ear Node Leaf (cm) | | | 7.8 | 0.63 | 10 |
| Length of Ear Node Leaf (cm) | | | 62.1 | 4.65 | 10 |
| Number of Leaves above Top Ear | | | 5.4 | 0.70 | 10 |
| Leaf Angle: (at anthesis, 2nd leaf above ear to stalk above leaf) (Degrees) | | | 25.2 | 3.82 | 10 |
| * Leaf Color: V. Dark Green Munsell: 7.5GY36 | | | | | |
| Leaf Sheath Pubescence: 1 = none to 9 = like peach fuzz | | | 3 | | |
| 5. TASSEL: | | | | | |
| Number of Primary Lateral Branches | | | 4.2 | 0.79 | 10 |
| Branch Angle from Central Spike | | | 37.8 | 7.57 | 10 |
| Tassel Length: (from peduncle node to tassel tip), (cm). | | | 49.7 | 2.98 | 10 |
| Pollen Shed: 0 = male sterile, 9 = heavy shed | | | 5 | | |
| * Anther Color: Pale Yellow Munsell: 2.5Y8.56 | | | | | |
| * Glume Color: Med. Green Munsell: 7.5GY56 | | | | | |
| * Bar Glumes (glume bands): 1 = absent, 2 = present | | | 1 | | |
| Peduncle Length: (from top leaf node to lower florets or branches), (cm). | | | 21.3 | 2.06 | 10 |
| * Munsell Glossy Book of Color, (A standard color reference). Kollmorgen Inst. Corp. New Windsor, NY. | | | | | |

TABLE 1-continued

VARIETY DESCRIPTION INFORMATION
PHF1J

| 6a. EAR (Unhusked ear) | AVG | STDEV | N |
|---|---|---|---|
| * Silk color: Light Green Munsell: 7.5Y8.54 | | | |
| (3 days after silk emergence) | | | |
| * Fresh husk color: Light Green Munsell: 5GY76 | | | |
| * Dry husk color: Buff Munsell: 2.5Y8.54 | | | |
| (65 days after 50% silking) | | | |
| Ear position at dry husk stage: 1 = upright, 2 = horizontal, | 1 | | |
| 3 = pendant | | | |
| Husk Tightness: (1 = very loose, 9 = very tight) | 6 | | |
| Husk Extension (at harvest): 1 = short (ears exposed), | 2 | | |
| 2 = medium (<8 cm), 3 = long (8-10 cm), 4 = v. long (>10 cm) | | | |
| 6b. EAR (Husked ear data) | | | |
| Ear Length (cm): | 12.7 | 0.48 | 10 |
| Ear Diameter at mid-point (mm) | 36.7 | 1.16 | 10 |
| Ear Weight (gm): | 83.8 | 6.39 | 10 |
| Number of Kernel Rows: | 13.6 | 1.84 | 10 |
| Kernel Rows: 1 = indistinct, 2 = distinct | 2 | | |
| Row Alignment: 1 = straight, 2 = slightly curved, 3 = spiral | 2 | | |
| Shank Length (cm): | 9.2 | 1.55 | 10 |
| Ear Taper: 1 = slight cylind., 2 = average, 3 = extreme conic. | 2 | | |
| 7. KERNEL (Dried) | | | |
| Kernel Length (mm): | 10.7 | 0.48 | 10 |
| Kernel Width (mm): | 7.9 | 0.74 | 10 |
| Kernel Thickness (mm): | 5.5 | 0.71 | 10 |
| Round Kernels (shape grade) (%) | 62.1 | 12.72 | 2 |
| Aleurone Color Pattern: 1 = homozygous, 2 = segregating | 1 | | |
| * Aleurone Color: Yellow Orange Munsell: 7.5YR716 | | | |
| * Hard Endo. Color: Yellow Orange Munsell: 7.5YR714 | | | |
| Endosperm Type: | 3 | | |
| 1 = sweet (su1), 2 = extra sweet (sh2), 3 = normal starch, | | | |
| 4 = high amylose starch, 5 = waxy starch, 6 = high protein, | | | |
| 7 = high lysine, 8 = super sweet (se), 9 = high oil, 10 = other | | | |
| Weight per 100 Kernels (unsized sample) (gm): | 29.5 | 0.71 | 2 |
| 8. COB: | | | |
| * Cob Diameter at mid-point (mm): | 20.5 | 1.08 | 10 |
| * Cob Color: White Munsell: 5Y91 | | | |
| * Munsell Glossy Book of color, (A standard color reference). Kollmorgen | | | |
| Inst. Corp. New Windsor, NY. | | | |

10. DISEASE RESISTANCE:
    (Rate from 1 = most-susceptable to 9 = most-resistant. Leave blank if not tested, leave race or strain options blank if polygenic.)

A. LEAF BLIGHTS, WILTS, AND LOCAL INFECTION DISEASES
    Anthracnose Leaf Blight (*Colletotrichum graminicola*)
    Common Rust (*Puccinia sorghi*)
    Common Smut (*Ustilago maydis*)
    Eyespot (*Kabatiella zeae*)
    Goss's Wilt (*Clavibacter michiganense* spp.
    Gray Leaf Spot (*Cercospora zeae-maydis*)
    Helminthosporium Leaf Spot (*Bipolaris zeicola*) Race:
    Northern Leaf Blight (*Exserohilum turcicum*) Race:
    Southern Leaf Blight (*Bipolaris maydis*) Race:
    Southern Rust (*Puccinia polysora*)
    Stewart's Wilt (*Erwinia stewartii*)
    Other (Specify):_____

B. SYSTEMIC DISEASES
    Corn Lethal Necrosis (MCMV and MDMV)
    Head Smut (*Sphacelotheca reiliana*)
    Maize Chlorotic Dwarf Virus (MDV)
    Maize Chlorotic Mottle Virus (MCMV)
    Maize Dwarf Mosaic Virus (MDMV)
    *Sorghum* Downy Mildew of Corn (*Peronosclerospora sorghi*)
    Other (Specify):_____

C. STALK ROTS
    Anthracnose Stalk Rot (*Colletotrichum graminicola*)
    Diplodia Stalk Rot (*Stenocarpella maydis*)
    *Fusarium* Stalk Rot (*Fusarium moniliforme*)
    *Gibberella* Stalk Rot (*Gibberella zeae*)
    Other (Specify):_____

D. EAR AND KERNEL ROTS
    *Aspergillus* Ear and Kernel Rot (*Aspergillus flavus*)
    Diplodia Ear Rot (*Stenocarpella maydis*)
    7  *Fusarium* Ear and Kernel Rot (*Fusarium moniliforme*)
    *Gibberella* Ear Rot (*Gibberella zeae*)
    Other (Specify):_____

TABLE 1-continued

VARIETY DESCRIPTION INFORMATION
PHF1J

11. INSECT RESISTANCE:
    (Rate from 1 = most-suscept. to 9 = most-resist., leave blank if not tested.)
    Corn Worm (*Helicoverpa zea*)
    ____ Leaf Feeding
    ____ Silk Feeding
    ____ Ear Damage
    Corn Leaf Aphid (*Rophalosiphum maydis*)
    Corn Sap Beetle (*Capophilus dimidiatus*)
    European Corn Borer (*Ostrinia nubilalis*)
    1st. Generation (Typically whorl leaf feeding)
    2nd. Generation (Typically leaf sheath-collar feeding)
    ____ Stalk Tunneling
    ____ cm tunneled/plant
    Fall armyworm (*Spodoptera fruqiperda*)
    ____ Leaf Feeding
    ____ Silk Feeding
    ____ mg larval wt.
    Maize Weevil (*Sitophilus zeamaize*)
    Northern Rootworm (*Diabrotica barberi*)
    Southern Rootworm (*Diabrotica undecimpunctata*)
    Southwestern Corn Borer (*Diatreaea grandiosella*)
    ____ Leaf Feeding
    ____ Stalk Tunneling
    ____ cm tunneled/plant
    Two-spotted Spider Mite (*Tetranychus utricae*)
    Western Rootworm (*Diabrotica virgifrea virgifrea*)
    Other (Specify):____
12. AGRONOMIC TRAITS:
    4   Staygreen (at 65 days after anthesis; rate from 1-worst to 9-excellent)
        % Dropped Ears (at 65 days after anthesis)
        % Pre-anthesis Brittle Snapping
        % Pre-anthesis Root Lodging
    3   % Post-anthesis Root Lodging (at 65 days after anthesis)
    3   % Post-anthesis Stalk Lodging
    4,103.0 Kg/ha (Yield at 12-13% grain moisture)

TABLE 2

SSR PROFILE DATA FOR PHF1J.

| Bin | Marker Name | Base Pairs |
|---|---|---|
| 1.01 | BNLG1014 | 126 |
| 1.01 | TUB1 | 252.3 |
| 1.01 | UMC1685 | 126.8 |
| 1.01 | UMC2012 | 86 |
| 1.01 | UMC2224 | 354.8 |
| 1.01 | UMC2225 | 313.4 |
| 1.02 | BNLG1127 | 116.4 |
| 1.02 | BNLG1429 | 211 |
| 1.02 | BNLG1953 | 252 |
| 1.02 | UMC1711 | 251.3 |
| 1.02 | UMC2204 | 133.3 |
| 1.02 | UMC2383 | 197.6 |
| 1.03 | PHI109275 | 142.9 |
| 1.03 | UMC1701 | 117.7 |
| 1.04 | BNLG1016 | 315.8 |
| 1.04 | BNLG2086 | 225 |
| 1.04 | BNLG2238 | 222.8 |
| 1.04 | UMC1144 | 230.2 |
| 1.04 | UMC1472 | 218.9 |
| 1.04 | UMC2228 | 218.6 |
| 1.04 | UMC2390 | 147.4 |
| 1.05 | UMC1244 | 343.8 |
| 1.05 | UMC1626 | 139.5 |
| 1.05 | UMC1703 | 153 |
| 1.05 | UMC1906 | 161.6 |
| 1.05 | UMC2025 | 131.2 |
| 1.05 | UMC2232 | 137 |
| 1.06 | BNLG1057 | 274 |
| 1.06 | UMC1035 | 213.9 |
| 1.06 | UMC1254 | 167.1 |
| 1.06 | UMC1398 | 164.2 |
| 1.06 | UMC1709 | 353.7 |
| 1.06 | UMC1919 | 156.9 |
| 1.06 | UMC1924 | 164.1 |
| 1.06 | UMC1988 | 347.4 |
| 1.06 | UMC2234 | 144.1 |
| 1.06 | UMC2237 | 161.7 |
| 1.07 | BNLG1556 | 203.9 |
| 1.07 | UMC1848 | 143.5 |
| 1.07 | UMC2387 | 112.1 |
| 1.08 | BNLG2228 | 224.4 |
| 1.08 | UMC1991 | 219.1 |
| 1.08 | UMC2029 | 158.1 |
| 1.08 | UMC2181 | 113.2 |
| 1.08 | UMC2240 | 239.8 |
| 1.08 | UMC2385 | 264.3 |
| 1.09 | BNLG1331 | 141.8 |
| 1.09 | GLB1 | 226.6 |
| 1.09 | UMC1715 | 137.8 |
| 1.09 | UMC2028 | 116.3 |
| 1.09 | UMC2047 | 133.3 |
| 1.1 | PHI308707 | 131.3 |
| 1.1 | UMC1885 | 142.6 |
| 1.1 | UMC2189 | 112.1 |
| 1.11 | PHI064 | 94.7 |
| 1.11 | PHI227562 | 306.8 |
| 1.11 | PHI265454 | 217.5 |
| 1.11 | UMC1500 | 249.4 |
| 1.11 | UMC1630 | 181.4 |
| 1.11 | UMC1681 | 138.4 |

TABLE 2-continued

SSR PROFILE DATA FOR PHF1J.

| Bin | Marker Name | Base Pairs |
|---|---|---|
| 1.11 | UMC2241 | 333.2 |
| 1.11 | UMC2242 | 344.9 |
| 1.12 | UMC1797 | 138.4 |
| 2.01 | PHI96100 | 280 |
| 2.01 | UMC2363 | 339.2 |
| 2.02 | BNLG1017 | 195.4 |
| 2.02 | UMC1265 | 311.4 |
| 2.02 | UMC1824A | 138.1 |
| 2.03 | BNLG1064 | 187.9 |
| 2.03 | UMC1845 | 158.5 |
| 2.03 | UMC2246 | 139 |
| 2.04 | PRP2 | 129.2 |
| 2.04 | UMC1326 | 142.9 |
| 2.04 | UMC1861 | 311.7 |
| 2.04 | UMC2007 | 106.9 |
| 2.04 | UMC2030 | 168.4 |
| 2.04 | UMC2032 | 164.5 |
| 2.04 | UMC2247 | 253.6 |
| 2.05 | UMC1459 | 107.1 |
| 2.05 | UMC1635 | 140.2 |
| 2.05 | UMC2252 | 108.4 |
| 2.05 | UMC2254 | 100.7 |
| 2.06 | BNLG1036 | 163.2 |
| 2.06 | BNLG1138 | 218.2 |
| 2.06 | BNLG1831 | 190.2 |
| 2.06 | UMC1004 | 160.6 |
| 2.06 | UMC1156 | 234.8 |
| 2.06 | UMC1658 | 142.4 |
| 2.06 | UMC1749 | 206.4 |
| 2.06 | UMC1946 | 78 |
| 2.06 | UMC2178 | 312.3 |
| 2.06 | UMC2192 | 334.9 |
| 2.06 | UMC2194 | 315.8 |
| 2.07 | PHI251315 | 124 |
| 2.07 | UMC1560 | 136.5 |
| 2.07 | UMC1637 | 114.9 |
| 2.07 | UMC2374 | 239.1 |
| 2.08 | BNLG1141 | 180.6 |
| 2.08 | BNLG1940 | 208.5 |
| 2.08 | PHI435417 | 216.9 |
| 2.08 | UMC1049 | 138.6 |
| 2.08 | UMC1126 | 133.3 |
| 2.08 | UMC1230 | 316.3 |
| 2.08 | UMC1745 | 216 |
| 2.08 | UMC1947 | 126.9 |
| 2.08 | UMC2202 | 335.3 |
| 2.09 | UMC1525 | 215.8 |
| 2.09 | UMC1551 | 240.7 |
| 2.1 | PHI101049 | 230.1 |
| 2.1 | UMC2214 | 287.5 |
| 3 | PHI453121 | 211.6 |
| 3 | UMC1931 | 99.3 |
| 3.01 | PHI404206 | 298.7 |
| 3.01 | UMC1892 | 105.6 |
| 3.01 | UMC2049 | 159.5 |
| 3.01 | UMC2255 | 216.9 |
| 3.01 | UMC2256 | 174.9 |
| 3.01 | UMC2376 | 149.4 |
| 3.01 | UMC2377 | 97.5 |
| 3.02 | BNLG1647 | 152.1 |
| 3.02 | PHI243966 | 212 |
| 3.02 | UMC1814 | 360.1 |
| 3.02 | UMC2258 | 147 |
| 3.04 | BNLG1019A | 172.2 |
| 3.04 | BNLG1638 | 198.9 |
| 3.04 | BNLG1816 | 289.7 |
| 3.04 | TPI4 | 157.9 |
| 3.04 | UMC1025 | 163.7 |
| 3.04 | UMC1347 | 228.4 |
| 3.04 | UMC1655 | 155.6 |
| 3.04 | UMC1683 | 84.8 |
| 3.04 | UMC1908 | 133.5 |
| 3.04 | UMC2002 | 108.5 |
| 3.04 | UMC2033 | 72.1 |
| 3.04 | UMC2261 | 148.2 |
| 3.04 | UMC2262 | 141.7 |
| 3.04 | UMC2263 | 393.4 |
| 3.04 | UMC2264 | 219.3 |
| 3.05 | BNLG1035 | 100.9 |
| 3.05 | UMC1300 | 164.5 |
| 3.05 | UMC1307 | 134.5 |
| 3.05 | UMC1907 | 117.3 |
| 3.05 | UMC1954 | 344.2 |
| 3.05 | UMC2020 | 123.3 |
| 3.05 | UMC2265 | 203.3 |
| 3.06 | BNLG1160 | 208.8 |
| 3.06 | BNLG1951 | 125 |
| 3.06 | BNLG2241 | 168.8 |
| 3.06 | PHI102228 | 135.6 |
| 3.06 | UMC1311 | 214.8 |
| 3.06 | UMC1644 | 167.3 |
| 3.06 | UMC1674 | 128.3 |
| 3.06 | UMC2270 | 142 |
| 3.07 | UMC1286 | 234.1 |
| 3.07 | UMC1659 | 121.9 |
| 3.07 | UMC2050 | 128.8 |
| 3.07 | UMC2273 | 238.6 |
| 3.08 | UMC1844 | 142.9 |
| 3.08 | UMC1915 | 94.9 |
| 3.08 | UMC2276 | 134.1 |
| 3.09 | BNLG1496 | 196.2 |
| 3.09 | UMC1641 | 208 |
| 3.09 | UMC1813 | 162.2 |
| 3.1 | UMC2048 | 314.9 |
| 4 | MTL1 | 139.6 |
| 4.01 | UMC1757 | 182.2 |
| 4.03 | ADH2 | 117.5 |
| 4.04 | ZP1 | 235 |
| 4.05 | BNLG1265 | 192.5 |
| 4.05 | BNLG1755 | 216.8 |
| 4.05 | GPC1 | 187.6 |
| 4.05 | UMC1175 | 282 |
| 4.05 | UMC1662 | 122.3 |
| 4.05 | UMC1851 | 118.2 |
| 4.05 | UMC1964 | 146.2 |
| 4.05 | UMC1969 | 65 |
| 4.05 | UMC2061 | 127.8 |
| 4.06 | BNLG2291 | 160.7 |
| 4.06 | UMC1869 | 151.2 |
| 4.06 | UMC1945 | 113.4 |
| 4.07 | UMC1194 | 162 |
| 4.07 | UMC1620 | 144.1 |
| 4.07 | UMC1651 | 95.4 |
| 4.07 | UMC1847 | 151.5 |
| 4.07 | UMC2038 | 135.3 |
| 4.08 | BNLG2162 | 151 |
| 4.08 | PDH1 | 110.8 |
| 4.08 | SSU1 | 288.5 |
| 4.08 | UMC1371 | 124.7 |
| 4.08 | UMC1418 | 147.9 |
| 4.08 | UMC1559 | 144.5 |
| 4.08 | UMC1612 | 104.8 |
| 4.08 | UMC1667 | 147 |
| 4.08 | UMC1834 | 163.4 |
| 4.08 | UMC1856 | 156.9 |
| 4.08 | UMC1899 | 111.6 |
| 4.08 | UMC2187 | 90.9 |
| 4.08 | UMC2188 | 168.1 |
| 4.09 | BNLG1565 | 239.7 |
| 4.09 | RPD3 | 168.1 |
| 4.09 | UMC1284 | 144.2 |
| 4.09 | UMC1328 | 161.2 |
| 4.09 | UMC1650 | 136.7 |
| 4.09 | UMC1940 | 134.5 |
| 4.09 | UMC1999 | 131.2 |
| 4.09 | UMC2046 | 115.9 |
| 4.1 | BNLG589 | 167.2 |
| 4.11 | BNLG1890 | 200.7 |
| 4.11 | CAT3 | 169.7 |
| 5 | UMC1240 | 213.6 |

TABLE 2-continued

SSR PROFILE DATA FOR PHF1J.

| Bin | Marker Name | Base Pairs |
|---|---|---|
| 5 | UMC2022 | 153.4 |
| 5 | UMC2292 | 137.6 |
| 5.01 | UMC2036 | 158.4 |
| 5.03 | UMC1315 | 159 |
| 5.03 | UMC1355 | 362.5 |
| 5.03 | UMC1475 | 259.9 |
| 5.03 | UMC1686 | 96.7 |
| 5.03 | UMC1692 | 157.5 |
| 5.03 | UMC1731 | 361.9 |
| 5.03 | UMC1784 | 332 |
| 5.03 | UMC1850 | 125.1 |
| 5.03 | UMC2035 | 110.7 |
| 5.03 | UMC2294 | 98.4 |
| 5.03 | UMC2295 | 121.2 |
| 5.03 | UMC2297 | 150.9 |
| 5.04 | UMC1092 | 134.4 |
| 5.04 | UMC1162 | 130.8 |
| 5.04 | UMC1629 | 117.4 |
| 5.04 | UMC1815 | 260.4 |
| 5.04 | UMC1860 | 158 |
| 5.04 | UMC2298 | 83.1 |
| 5.04 | UMC2299 | 125.5 |
| 5.04 | UMC2302 | 348.5 |
| 5.04 | UMC2400 | 211.6 |
| 5.04 | UMC2407 | 210.2 |
| 5.05 | PHI333597 | 216.3 |
| 5.05 | UMC1687 | 152.4 |
| 5.05 | UMC1800 | 147.8 |
| 5.05 | UMC1853 | 113.5 |
| 5.05 | UMC2026 | 96.6 |
| 5.06 | GLN4 | 256.7 |
| 5.06 | UMC1941 | 113.2 |
| 5.06 | UMC2305 | 164.4 |
| 5.06 | UMC2306 | 103.4 |
| 5.07 | BNLG1118 | 64.2 |
| 5.07 | UMC1375 | 150.1 |
| 5.07 | UMC1537 | 329.6 |
| 5.07 | UMC2013 | 128.8 |
| 5.07 | UMC2198 | 141.6 |
| 5.09 | UMC2209 | 168.6 |
| 6 | UMC1753 | 216.2 |
| 6 | UMC1883 | 84.1 |
| 6.01 | CYC3 | 268.9 |
| 6.01 | UMC1195 | 135.6 |
| 6.01 | UMC1376 | 255.6 |
| 6.01 | UMC1625 | 137.2 |
| 6.01 | UMC2056 | 163.7 |
| 6.02 | SAUR1 | 113.4 |
| 6.02 | UMC1656 | 133.5 |
| 6.03 | UMC1887 | 99.1 |
| 6.04 | UMC1857 | 150.7 |
| 6.04 | UMC1918 | 167.3 |
| 6.04 | UMC2006 | 117.3 |
| 6.04 | UMC2317 | 129.6 |
| 6.05 | BNLG1174 | 222.8 |
| 6.05 | ROA2 | 354.4 |
| 6.05 | UMC1314 | 342.1 |
| 6.05 | UMC1352 | 148.7 |
| 6.05 | UMC1795 | 125.1 |
| 6.05 | UMC1805 | 126.4 |
| 6.06 | UMC1462 | 212.1 |
| 6.06 | UMC1859 | 95 |
| 6.06 | UMC1912 | 162.5 |
| 6.07 | BNLG1740 | 236.6 |
| 6.07 | BNLG1759A | 128.1 |
| 6.07 | PHI299852 | 116.7 |
| 6.07 | TLK1 | 83 |
| 6.07 | UMC1350 | 120.3 |
| 6.07 | UMC1653 | 198.2 |
| 6.07 | UMC1897 | 156.9 |
| 6.08 | UMC2059 | 127.1 |
| 7 | UMC1378 | 126.2 |
| 7.01 | UMC1159 | 230.1 |
| 7.02 | BNLG1094 | 171.3 |
| 7.02 | CYP6 | 119.6 |
| 7.02 | KPP1 | 304.8 |
| 7.02 | UMC1339 | 141.8 |
| 7.02 | UMC1929 | 161.2 |
| 7.02 | UMC1978 | 108.4 |
| 7.02 | UMC2327 | 114.3 |
| 7.03 | BNLG1070 | 145.4 |
| 7.03 | UMC1324 | 214.8 |
| 7.03 | UMC1660 | 204.6 |
| 7.03 | UMC1713 | 139.5 |
| 7.03 | UMC1841 | 111.3 |
| 7.04 | PHI328175 | 128 |
| 7.04 | UMC1342 | 219 |
| 7.04 | UMC1710 | 235.3 |
| 7.04 | UMC1799 | 104.2 |
| 7.05 | PHI069 | 195.2 |
| 7.06 | PHI116 | 169 |
| 8.01 | UMC2042 | 107.8 |
| 8.02 | UMC1304 | 246.4 |
| 8.02 | UMC1790 | 155.8 |
| 8.02 | UMC1913 | 162 |
| 8.02 | UMC1974 | 441.8 |
| 8.02 | UMC2004 | 130.4 |
| 8.03 | BNLG1863 | 213.3 |
| 8.03 | PHI100175 | 141.7 |
| 8.03 | PHI121 | 93.6 |
| 8.03 | UMC1289 | 221.6 |
| 8.03 | UMC1377 | 216.1 |
| 8.03 | UMC1735 | 104.1 |
| 8.03 | UMC1904 | 134.2 |
| 8.04 | BNLG2046 | 326.5 |
| 8.04 | UMC1343 | 317.1 |
| 8.04 | UMC1858 | 127.8 |
| 8.05 | BNLG1176 | 218.2 |
| 8.05 | UMC1141 | 312.9 |
| 8.05 | UMC1287 | 312.6 |
| 8.05 | UMC1316 | 233.1 |
| 8.05 | UMC1340 | 212.3 |
| 8.05 | UMC1846 | 106 |
| 8.05 | UMC1889 | 113.5 |
| 8.05 | UMC1959 | 330 |
| 8.06 | BNLG1031 | 291.8 |
| 8.06 | UMC1149 | 227 |
| 8.06 | UMC1161 | 253.9 |
| 8.07 | BNLG1065 | 237.1 |
| 8.08 | GST1 | 81.5 |
| 8.08 | UMC1933 | 112.5 |
| 8.08 | UMC2052 | 143 |
| 8.09 | PHI233376 | 135.7 |
| 8.09 | UMC1638 | 147.6 |
| 8.09 | UMC1663 | 186.1 |
| 9.01 | BNLG1810 | 205.2 |
| 9.01 | SH1 | 249 |
| 9.01 | UMC1040 | 237.1 |
| 9.01 | UMC1370 | 322.1 |
| 9.01 | UMC1809 | 230.2 |
| 9.01 | UMC1867 | 232.5 |
| 9.02 | UMC1131 | 362.3 |
| 9.02 | UMC1170 | 232.7 |
| 9.02 | UMC1636 | 195.3 |
| 9.02 | UMC1698 | 113.3 |
| 9.02 | UMC1893 | 102.3 |
| 9.02 | UMC2213 | 106.3 |
| 9.02 | UMC2336 | 264.5 |
| 9.03 | UMC1634 | 113.9 |
| 9.03 | UMC1688 | 310.6 |
| 9.03 | UMC1691 | 149.5 |
| 9.03 | UMC2337 | 118 |
| 9.03 | WX1 | 232.9 |
| 9.04 | BNLG1012 | 161.5 |
| 9.04 | BNLG1159B | 145.8 |
| 9.04 | UMC1519 | 256.5 |
| 9.04 | UMC2398 | 126.2 |
| 9.05 | MMP179 | 161.4 |
| 9.05 | UMC1357 | 257.2 |
| 9.05 | UMC1654 | 111.3 |

TABLE 2-continued

SSR PROFILE DATA FOR PHF1J.

| Bin | Marker Name | Base Pairs |
|---|---|---|
| 9.05 | UMC1657 | 159.3 |
| 9.05 | UMC1794 | 118.5 |
| 9.05 | UMC2338 | 110.9 |
| 9.05 | UMC2341 | 130.2 |
| 9.06 | PHI448880 | 185.8 |
| 9.06 | UMC1310 | 241.5 |
| 9.06 | UMC2207 | 115.4 |
| 9.06 | UMC2346 | 302.6 |
| 9.07 | BNLG619 | 273 |
| 9.07 | DUPSSR29 | 134.4 |
| 9.07 | UMC1104 | 207.6 |
| 9.07 | UMC1675 | 162.2 |
| 9.07 | UMC1714 | 161.6 |
| 9.07 | UMC1942 | 134.7 |
| 9.07 | UMC2347 | 136.2 |
| 9.08 | BNLG1129 | 298.6 |
| 10 | PHI041 | 203 |
| 10.01 | UMC2018 | 151.6 |
| 10.01 | UMC2053 | 103.7 |
| 10.02 | PHI059 | 143.3 |
| 10.02 | UMC1337 | 307.5 |
| 10.02 | UMC1432 | 119.1 |
| 10.02 | UMC1582 | 314.7 |
| 10.02 | UMC2034 | 132.9 |
| 10.02 | UMC2069 | 375.2 |
| 10.03 | BNLG1079 | 172.3 |
| 10.03 | BNLG1655 | 147.3 |
| 10.03 | UMC1312 | 315.6 |
| 10.03 | UMC1336 | 297.6 |
| 10.03 | UMC1345 | 163.5 |
| 10.03 | UMC1367 | 315.5 |
| 10.03 | UMC1381 | 213.4 |
| 10.03 | UMC1863 | 140.9 |
| 10.03 | UMC1938 | 160.4 |
| 10.03 | UMC1962 | 145.3 |
| 10.03 | UMC2016 | 125.1 |
| 10.03 | UMC2067 | 165.3 |
| 10.03 | UMC2348 | 222.2 |
| 10.04 | UMC1330 | 340.6 |
| 10.04 | UMC1589 | 114 |
| 10.04 | UMC1648 | 139.3 |
| 10.04 | UMC1697 | 96.6 |
| 10.04 | UMC1911 | 159.9 |
| 10.04 | UMC1930 | 124.9 |
| 10.04 | UMC2003 | 89.2 |
| 10.05 | BNLG1074 | 172 |
| 10.06 | BNLG1028 | 133.9 |
| 10.07 | BNLG1450 | 184.9 |
| 10.07 | BNLG1839 | 198.2 |
| 10.07 | UMC1038 | 261.1 |
| 10.07 | UMC1556 | 254.5 |
| 10.07 | UMC1640 | 103.7 |
| 10.07 | UMC1645 | 164 |
| 10.07 | UMC2021 | 127.9 |

TABLE 3A

PAIRED INBRED COMPARISON REPORT
Variety #1: PHF1J
Variety #2: PH5TG

| Stat | YIELD BU/A 56# ABS | YIELD BU/A 56# % MN | MST PCT ABS | TSTWT LB/BU ABS | EGRWTH SCORE ABS | ESTCNT COUNT ABS | TILLER PCT ABS | GDUSHD GDU ABS | GDUSLK GDU ABS | POLWT VALUE ABS |
|---|---|---|---|---|---|---|---|---|---|---|
| Mean1 | 65.5 | 69.9 | 21.0 | 53.1 | 6.3 | 45.4 | 1.4 | 120.0 | 121.9 | 29.7 |
| Mean2 | 103.0 | 107.9 | 19.3 | 59.0 | 6.2 | 42.9 | 4.6 | 120.5 | 125.8 | 79.6 |
| Locs | 34 | 34 | 37 | 3 | 10 | 24 | 13 | 33 | 33 | 4 |
| Reps | 63 | 63 | 66 | 6 | 11 | 47 | 13 | 35 | 35 | 7 |
| Diff | -37.6 | -38.0 | -1.7 | -5.8 | 0.1 | 2.5 | 3.2 | -0.6 | -3.9 | -49.9 |
| Prob | 0.000 | 0.000 | 0.007 | 0.453 | 0.591 | 0.031 | 0.226 | 0.342 | 0.000 | 0.029 |

| Stat | POLWT VALUE % MN | TASBLS SCORE ABS | TASSZ SCORE ABS | PLTHT CM ABS | EARHT CM ABS | STAGRN SCORE ABS | SCTGRN SCORE ABS | BARPLT % NOT ABS | FUSERS SCORE ABS | COMRST SCORE ABS |
|---|---|---|---|---|---|---|---|---|---|---|
| Mean1 | 24.1 | 9.0 | 4.0 | 192.0 | 81.5 | 6.5 | 5.9 | 83.0 | 7.3 | 5.0 |
| Mean2 | 64.9 | 9.0 | 4.3 | 207.4 | 84.7 | 6.0 | 7.6 | 96.6 | 8.3 | 5.0 |
| Locs | 4 | 1 | 25 | 24 | 14 | 2 | 8 | 24 | 7 | 1 |
| Reps | 7 | 1 | 25 | 26 | 16 | 2 | 12 | 31 | 11 | 1 |
| Diff | -40.8 | 0.0 | -0.3 | -15.3 | -3.2 | 0.5 | -1.8 | -13.6 | -1.0 | 0.0 |
| Prob | 0.022 | . | 0.175 | 0.000 | 0.275 | 0.500 | 0.035 | 0.005 | 0.221 | . |

| Stat | ECBDPE % NOT ABS | ECB2SC SCORE ABS | CLDTST PCT ABS | CLDTST PCT % MN | KSZDCD PCT ABS | ERTLPN % NOT ABS | LRTLPN % NOT ABS | STLPCN % NOT ABS |
|---|---|---|---|---|---|---|---|---|
| Mean1 | 100.0 | 9.0 | 92.4 | 99.2 | 7.3 | 95.7 | 97.8 | 98.8 |
| Mean2 | 93.4 | 5.5 | 92.9 | 99.8 | 6.1 | 100.0 | 87.5 | 100.0 |
| Locs | 1 | 1 | 20 | 20 | 26 | 3 | 2 | 4 |
| Reps | 2 | 2 | 25 | 25 | 37 | 4 | 2 | 7 |
| Diff | 6.6 | 3.5 | -0.6 | -0.5 | 1.2 | -4.3 | 10.3 | -1.3 |
| Prob | . | . | 0.805 | 0.836 | 0.249 | 0.423 | 0.500 | 0.391 |

TABLE 3B

PAIRED INBRED COMPARISON REPORT
Variety #1: PHF1J
Variety #2: PHAA0

| Stat | YIELD BU/A 56# ABS | YIELD BU/A 56# % MN | MST PCT ABS | TSTWT LB/BU ABS | EGRWTH SCORE ABS | ESTCNT COUNT ABS | TILLER PCT ABS | GDUSHD GDU ABS |
|---|---|---|---|---|---|---|---|---|
| Mean1 | 73.1 | 76.7 | 20.5 | 57.9 | 6.5 | 37.1 | 1.1 | 119.3 |
| Mean2 | 96.7 | 102.1 | 17.4 | 58.0 | 6.0 | 33.8 | 0.9 | 116.2 |
| Locs | 7 | 7 | 7 | 2 | 15 | 21 | 13 | 46 |
| Reps | 12 | 12 | 12 | 3 | 15 | 22 | 13 | 46 |
| Diff | −23.7 | −25.4 | −3.1 | 0.0 | 0.5 | 3.4 | −0.1 | 3.1 |
| Prob | 0.006 | 0.003 | 0.031 | 0.972 | 0.187 | 0.047 | 0.872 | 0.000 |

| Stat | GDUSLK GDU ABS | TASBLS SCORE ABS | TASSZ SCORE ABS | PLTHT CM ABS | EARHT CM ABS | STAGRN SCORE ABS | SCTGRN SCORE ABS | BARPLT % NOT ABS |
|---|---|---|---|---|---|---|---|---|
| Mean1 | 121.0 | 9.0 | 4.0 | 190.1 | 86.1 | 5.0 | 6.5 | 81.3 |
| Mean2 | 117.4 | 9.0 | 3.2 | 196.8 | 85.0 | 4.3 | 9.0 | 96.5 |
| Locs | 46 | 1 | 39 | 31 | 18 | 3 | 4 | 20 |
| Reps | 46 | 1 | 39 | 31 | 18 | 3 | 4 | 20 |
| Diff | 3.6 | 0.0 | 0.8 | −6.6 | 1.1 | 0.7 | −2.5 | −15.1 |
| Prob | 0.000 | . | 0.000 | 0.074 | 0.728 | 0.423 | 0.063 | 0.002 |

| Stat | GLFSPT SCORE ABS | NLFBLT SCORE ABS | GOSWLT SCORE ABS | FUSERS SCORE ABS | GIBERS SCORE ABS | EYESPT SCORE ABS | COMRST SCORE ABS | ECBDPE % NOT ABS |
|---|---|---|---|---|---|---|---|---|
| Mean1 | 4.3 | 4.0 | 5.0 | 8.3 | 5.5 | 6.5 | 6.7 | 100.0 |
| Mean2 | 2.8 | 7.0 | 5.0 | 9.0 | 6.0 | 6.0 | 5.7 | 94.9 |
| Locs | 3 | 1 | 1 | 3 | 1 | 1 | 3 | 1 |
| Reps | 6 | 1 | 2 | 3 | 2 | 2 | 3 | 2 |
| Diff | 1.5 | −3.0 | 0.0 | −0.7 | −0.5 | 0.5 | 1.0 | 5.1 |
| Prob | 0.356 | . | . | 0.423 | . | . | 0.225 | . |

| Stat | CLDTST PCT ABS | CLDTST PCT % MN | KSZDCD PCT ABS | ERTLPN % NOT ABS | LRTLPN % NOT ABS | STLLPN % NOT ABS | STLPCN % NOT ABS |
|---|---|---|---|---|---|---|---|
| Mean1 | 94.8 | 98.8 | 6.6 | 95.7 | 100.0 | 96.0 | 98.8 |
| Mean2 | 94.4 | 98.3 | 8.0 | 100.0 | 100.0 | 85.0 | 98.8 |
| Locs | 5 | 5 | 5 | 3 | 1 | 2 | 4 |
| Reps | 5 | 5 | 5 | 3 | 1 | 3 | 5 |
| Diff | 0.4 | 0.5 | −1.3 | −4.3 | 0.0 | 11.0 | 0.0 |
| Prob | 0.847 | 0.829 | 0.399 | 0.423 | . | 0.666 | 1.000 |

TABLE 3C

PAIRED INBRED COMPARISON REPORT
Variety #1: PHF1J
Variety #2: PH0AV

| Stat | YIELD BU/A 56# ABS | YIELD BU/A 56# % MN | MST PCT ABS | TSTWT LB/BU ABS | EGRWTH SCORE ABS | ESTCNT COUNT ABS | TILLER PCT ABS | GDUSHD GDU ABS | GDUSLK GDU ABS | POLWT VALUE ABS | POLWT VALUE % MN |
|---|---|---|---|---|---|---|---|---|---|---|---|
| Mean1 | 56.5 | 61.5 | 17.9 | 51.2 | 6.7 | 34.3 | 1.4 | 118.2 | 119.8 | 86.1 | 75.8 |
| Mean2 | 66.4 | 70.7 | 17.0 | 56.0 | 5.9 | 33.5 | 1.6 | 121.9 | 122.4 | 97.1 | 85.4 |
| Locs | 15 | 15 | 16 | 2 | 15 | 27 | 22 | 70 | 69 | 25 | 25 |
| Reps | 29 | 29 | 30 | 4 | 19 | 34 | 22 | 78 | 77 | 50 | 50 |
| Diff | −10.0 | −9.2 | −0.9 | −4.9 | 0.7 | 0.8 | 0.1 | −3.7 | −2.6 | −11.0 | −9.6 |
| Prob | 0.083 | 0.125 | 0.140 | 0.659 | 0.023 | 0.628 | 0.813 | 0.041 | 0.149 | 0.056 | 0.059 |

| Stat | TASBLS SCORE ABS | TASSZ SCORE ABS | PLTHT CM ABS | EARHT CM ABS | STAGRN SCORE ABS | SCTGRN SCORE ABS | TEXEAR SCORE ABS | BARPLT % NOT ABS | GLFSPT SCORE ABS | NLFBLT SCORE ABS | GOSWLT SCORE ABS |
|---|---|---|---|---|---|---|---|---|---|---|---|
| Mean1 | 9.0 | 3.9 | 193.3 | 87.5 | 4.6 | 6.5 | 4.5 | 81.6 | 4.3 | 5.0 | 5.0 |
| Mean2 | 9.0 | 4.4 | 197.4 | 88.6 | 5.4 | 8.8 | 2.0 | 92.4 | 6.8 | 7.0 | 4.5 |
| Locs | 3 | 57 | 43 | 29 | 5 | 4 | 2 | 30 | 3 | 1 | 1 |
| Reps | 3 | 65 | 46 | 32 | 5 | 4 | 2 | 30 | 6 | 1 | 2 |
| Diff | 0.0 | −0.5 | −4.2 | −1.1 | −0.8 | −2.3 | 2.5 | −10.9 | −2.5 | −2.0 | 0.5 |
| Prob | 1.000 | 0.001 | 0.065 | 0.674 | 0.242 | 0.058 | 0.126 | 0.001 | 0.138 | . | . |

TABLE 3C-continued

PAIRED INBRED COMPARISON REPORT
Variety #1: PHF1J
Variety #2: PH0AV

| Stat | FUSERS SCORE ABS | GIBERS SCORE ABS | EYESPT SCORE ABS | COMRST SCORE ABS | CLDTST PCT ABS | CLDTST PCT % MN | KSZDCD PCT ABS | ERTLPN % NOT ABS | LRTLPN % NOT ABS | STLLPN % NOT ABS | STLPCN % NOT ABS |
|---|---|---|---|---|---|---|---|---|---|---|---|
| Mean1 | 7.5 | 5.5 | 6.5 | 5.0 | 95.0 | 101.0 | 5.9 | 100.0 | 98.5 | 96.0 | 100.0 |
| Mean2 | 6.5 | 4.5 | 6.0 | 8.0 | 93.3 | 99.0 | 14.0 | 100.0 | 96.7 | 73.3 | 100.0 |
| Locs | 6 | 1 | 1 | 1 | 7 | 7 | 7 | 3 | 3 | 2 | 1 |
| Reps | 6 | 2 | 2 | 1 | 7 | 7 | 7 | 3 | 4 | 3 | 1 |
| Diff | 1.0 | 1.0 | 0.5 | -3.0 | 1.7 | 1.9 | -8.1 | 0.0 | 1.8 | 22.8 | 0.0 |
| Prob | 0.111 | . | . | . | 0.399 | 0.389 | 0.004 | 1.000 | 0.423 | 0.258 | . |

TABLE 4

GENERAL COMBINING ABILITY REPORT FOR PHF1J

| | | |
|---|---|---|
| PRM Day ABS | Mean | 94 |
| PRM Day ABS | Reps | 4482 |
| PRMSHD Day ABS | Mean | 93 |
| PRMSHD Day ABS | Reps | 4192 |
| YIELD bu/a 56# ABS | Mean | 181.2 |
| YIELD bu/a 56# ABS | Reps | 2358 |
| YIELD bu/a 56# ABS | Years | 3 |
| YIELD bu/a 56# % MN | Mean | 100.3 |
| YIELD bu/a 56# % MN | Reps | 2358 |
| MST pct ABS | Mean | 23.4 |
| MST pct ABS | Reps | 2366 |
| MST pct % MN | Mean | 99.7 |
| MST pct % MN | Reps | 2366 |
| YLDMST ABS | Mean | 100.5 |
| YLDMST ABS | Reps | 2493 |
| STLPCN % NOT % MN | Mean | 102 |
| STLPCN % NOT % MN | Reps | 309 |
| STLLPN % NOT % MN | Mean | 104 |
| STLLPN % NOT % MN | Reps | 345 |
| ERTLPN % NOT % MN | Mean | 99 |
| ERTLPN % NOT % MN | Reps | 129 |
| LRTLPN % NOT % MN | Mean | 99 |
| LRTLPN % NOT % MN | Reps | 449 |
| TSTWT lb/bu % MN | Mean | 100.6 |
| TSTWT lb/bu % MN | Reps | 1353 |
| STKCNT count % MN | Mean | 100 |
| STKCNT count % MN | Reps | 4202 |
| PLTHT in % MN | Mean | 100 |
| PLTHT in % MN | Reps | 1027 |
| EARHT in % MN | Mean | 102 |
| EARHT in % MN | Reps | 1028 |
| BRTSTK % NOT % MN | Mean | 101 |
| BRTSTK % NOT % MN | Reps | 29 |
| BORBMN % NOT % MN | Mean | 103 |
| BORBMN % NOT % MN | Reps | 108 |
| BRENGMN kg * mm % MN | Mean | 97.1 |
| BRENGMN kg * mm % MN | Reps | 49 |
| GLFSPT score ABS | Mean | 5 |
| GLFSPT score ABS | Reps | 59 |
| STAGRN score ABS | Mean | 5 |
| STAGRN score ABS | Reps | 497 |
| HSKCVR score ABS | Mean | 6 |
| HSKCVR score ABS | Reps | 227 |
| ECBLSI score ABS | Mean | 5.5 |
| ECBLSI score ABS | Reps | 66 |

TABLE 5A

INBREDS IN HYBRID COMBINATION REPORT
Variety #1: HYBRID CONTAINING PHF1J
Variety #2: 38P04

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT CM % MN |
|---|---|---|---|---|---|---|---|---|---|
| Mean1 | 182.6 | 102.5 | 95.9 | 113.6 | 116.8 | 99.1 | 97.2 | 100.2 | 98.4 |
| Mean2 | 178.3 | 100.0 | 97.0 | 95.2 | 68.3 | 100.1 | 99.7 | 99.9 | 98.7 |
| Locs | 103 | 103 | 105 | 19 | 2 | 41 | 28 | 173 | 44 |
| Reps | 110 | 110 | 112 | 19 | 3 | 49 | 34 | 249 | 45 |
| Diff | 4.3 | 2.5 | 1.1 | 18.4 | 48.5 | -1.0 | -2.5 | 0.3 | -0.3 |
| Prob | 0.008 | 0.008 | 0.106 | 0.000 | 0.424 | 0.011 | 0.000 | 0.208 | 0.676 |

| Stat | EARHT CM % MN | STAGRN SCORE % MN | STKLDG % NOT % MN | STLLPN % NOT % MN | DRPEAR % NOT % MN | TSTWT LB/BU ABS | GLFSPT SCORE ABS | NLFBLT SCORE ABS | GOSWLT SCORE ABS |
|---|---|---|---|---|---|---|---|---|---|
| Mean1 | 100.4 | 111.3 | 105.8 | 111.9 | 100.2 | 55.4 | 5.0 | 6.0 | 5.5 |
| Mean2 | 97.9 | 98.3 | 97.9 | 93.2 | 100.2 | 54.7 | 3.8 | 6.7 | 6.3 |
| Locs | 43 | 38 | 3 | 23 | 3 | 89 | 3 | 4 | 2 |
| Reps | 44 | 42 | 4 | 51 | 3 | 93 | 6 | 8 | 4 |
| Diff | 2.4 | 13.0 | 7.9 | 18.7 | 0.0 | 0.7 | 1.2 | -0.7 | -0.8 |
| Prob | 0.069 | 0.011 | 0.140 | 0.014 | 1.000 | 0.000 | 0.192 | 0.122 | 0.205 |

TABLE 5A-continued

INBREDS IN HYBRID COMBINATION REPORT
Variety #1: HYBRID CONTAINING PHF1J
Variety #2: 38P04

| Stat | ECB1LF SCORE ABS | ECB2SC SCORE ABS | HSKCVR SCORE ABS | GIBROT SCORE ABS | BRTSTK % NOT ABS | ERTLPN % NOT ABS | LRTLPN % NOT ABS | STLPCN % NOT ABS |
|---|---|---|---|---|---|---|---|---|
| Mean1 | 9.0 | 9.0 | 6.3 | 8.0 | 92.3 | 72.8 | 77.9 | 96.1 |
| Mean2 | 9.0 | 9.0 | 6.4 | 4.8 | 90.6 | 68.9 | 81.9 | 89.2 |
| Locs | 2 | 2 | 13 | 2 | 6 | 10 | 10 | 26 |
| Reps | 4 | 4 | 15 | 4 | 6 | 15 | 11 | 27 |
| Diff | 0.0 | 0.0 | −0.1 | 3.3 | 1.7 | 3.9 | −4.0 | 6.9 |
| Prob | 1.000 | 1.000 | 0.621 | 0.049 | 0.455 | 0.386 | 0.393 | 0.000 |

TABLE 5B

INBREDS IN HYBRID COMBINATION REPORT
Variety #1: HYBRID CONTAINING PHF1J
Variety #2: 38K35

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT CM % MN |
|---|---|---|---|---|---|---|---|---|---|
| Mean1 | 183.4 | 99.4 | 98.7 | 118.7 | 132.7 | 98.6 | 97.5 | 100.9 | 98.9 |
| Mean2 | 178.2 | 96.5 | 96.2 | 87.6 | 113.6 | 97.5 | 98.4 | 100.5 | 102.4 |
| Locs | 102 | 102 | 105 | 8 | 2 | 31 | 26 | 146 | 39 |
| Reps | 165 | 165 | 168 | 9 | 4 | 46 | 37 | 264 | 59 |
| Diff | 5.2 | 2.9 | −2.5 | 31.1 | 19.1 | 1.1 | −0.9 | 0.4 | −3.5 |
| Prob | 0.003 | 0.004 | 0.000 | 0.000 | 0.273 | 0.005 | 0.048 | 0.091 | 0.000 |

| Stat | EARHT CM % MN | STAGRN SCORE % MN | STKLDG % NOT % MN | STLLPN % NOT % MN | DRPEAR % NOT % MN | TSTWT LB/BU ABS | GLFSPT SCORE ABS | NLFBLT SCORE ABS | GOSWLT SCORE ABS |
|---|---|---|---|---|---|---|---|---|---|
| Mean1 | 100.8 | 111.1 | 105.1 | 111.0 | 100.3 | 56.7 | 4.5 | 5.8 | 5.5 |
| Mean2 | 106.4 | 68.7 | 97.7 | 87.5 | 100.3 | 56.8 | 3.1 | 2.0 | 5.1 |
| Locs | 39 | 34 | 2 | 23 | 5 | 93 | 4 | 3 | 4 |
| Reps | 59 | 54 | 3 | 49 | 7 | 149 | 8 | 6 | 8 |
| Diff | −5.6 | 42.4 | 7.4 | 23.5 | 0.0 | −0.1 | 1.4 | 3.8 | 0.4 |
| Prob | 0.000 | 0.000 | 0.500 | 0.001 | 1.000 | 0.578 | 0.076 | 0.013 | 0.718 |

| Stat | ECB1LF SCORE ABS | ECB2SC SCORE ABS | HSKCVR SCORE ABS | GIBROT SCORE ABS | BRTSTK % NOT ABS | ERTLPN % NOT ABS | LRTLPN % NOT ABS | STLPCN % NOT ABS |
|---|---|---|---|---|---|---|---|---|
| Mean1 | 9.0 | 9.0 | 6.5 | 5.8 | 99.5 | 74.8 | 72.7 | 93.3 |
| Mean2 | 9.0 | 8.9 | 6.3 | 3.3 | 100.0 | 65.7 | 64.8 | 83.6 |
| Locs | 4 | 4 | 14 | 2 | 3 | 8 | 15 | 12 |
| Reps | 8 | 8 | 20 | 4 | 4 | 14 | 25 | 19 |
| Diff | 0.0 | 0.1 | 0.1 | 2.5 | −0.5 | 9.1 | 7.9 | 9.7 |
| Prob | 1.000 | 0.391 | 0.704 | 0.126 | 0.423 | 0.019 | 0.127 | 0.002 |

TABLE 5C

INBREDS IN HYBRID COMBINATION REPORT
Variety #1: HYBRID CONTAINING PHF1J
Variety #2: 38W22

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT CM % MN | EARHT CM % MN |
|---|---|---|---|---|---|---|---|---|---|---|
| Mean1 | 183.8 | 100.5 | 97.3 | 115.3 | 123.6 | 98.9 | 97.5 | 100.5 | 98.6 | 100.4 |
| Mean2 | 175.2 | 95.9 | 93.7 | 95.9 | 90.4 | 96.8 | 97.1 | 100.4 | 100.3 | 103.7 |
| Locs | 142 | 142 | 146 | 16 | 3 | 50 | 39 | 219 | 55 | 55 |
| Reps | 207 | 207 | 211 | 17 | 5 | 68 | 51 | 372 | 75 | 75 |
| Diff | 8.5 | 4.6 | −3.6 | 19.4 | 33.2 | 2.1 | 0.4 | 0.1 | −1.7 | −3.3 |
| Prob | 0.000 | 0.000 | 0.000 | 0.000 | 0.047 | 0.000 | 0.165 | 0.552 | 0.002 | 0.006 |

TABLE 5C-continued

INBREDS IN HYBRID COMBINATION REPORT
Variety #1: HYBRID CONTAINING PHF1J
Variety #2: 38W22

| Stat | STAGRN SCORE % MN | STKLDG % NOT % MN | STLLPN % NOT % MN | DRPEAR % NOT % MN | TSTWT LB/BU ABS | GLFSPT SCORE ABS | NLFBLT SCORE ABS | GOSWLT SCORE ABS | GIBERS SCORE ABS | COMRST SCORE ABS |
|---|---|---|---|---|---|---|---|---|---|---|
| Mean1 | 112.2 | 105.8 | 112.5 | 100.3 | 56.2 | 4.8 | 6.1 | 5.5 | 6.0 | 6.0 |
| Mean2 | 65.9 | 87.6 | 84.4 | 100.3 | 56.7 | 2.6 | 2.3 | 6.0 | 8.0 | 5.0 |
| Locs | 53 | 3 | 30 | 5 | 127 | 5 | 5 | 4 | 1 | 1 |
| Reps | 75 | 5 | 68 | 7 | 184 | 10 | 11 | 7 | 1 | 1 |
| Diff | 46.3 | 18.2 | 28.0 | 0.0 | −0.5 | 2.2 | 3.8 | −0.5 | −2.0 | 1.0 |
| Prob | 0.000 | 0.269 | 0.000 | 1.000 | 0.000 | 0.017 | 0.003 | 0.613 | . | . |

| Stat | ECB1LF SCORE ABS | ECB2SC SCORE ABS | HSKCVR SCORE ABS | GIBROT SCORE ABS | BRTSTK % NOT ABS | ERTLPN % NOT ABS | LRTLPN % NOT ABS | STLPCN % NOT ABS |
|---|---|---|---|---|---|---|---|---|
| Mean1 | 9.0 | 9.0 | 6.4 | 6.8 | 99.6 | 78.4 | 77.3 | 94.7 |
| Mean2 | 9.0 | 7.9 | 5.7 | 5.0 | 98.3 | 61.5 | 66.9 | 83.0 |
| Locs | 4 | 4 | 20 | 3 | 4 | 13 | 18 | 22 |
| Reps | 8 | 8 | 28 | 6 | 5 | 21 | 29 | 30 |
| Diff | 0.0 | 1.1 | 0.6 | 1.8 | 1.3 | 17.0 | 10.3 | 11.7 |
| Prob | 1.000 | 0.078 | 0.001 | 0.128 | 0.527 | 0.016 | 0.060 | 0.002 |

TABLE 6

PHENOTYPIC DATA FROM HYBRIDS PRODUCED WITH PHF1J.

| | PRM Day ABS MEAN | PRM Day ABS REPS | PRM SHD Day ABS MEAN | PRM SHD Day ABS REPS | YIELD bu/a 56# ABS MEAN | YIELD bu/a 56# ABS REPS | YIELD bu/a 56# ABS YRS | YIELD bu/a 56# % MN MEAN | YIELD bu/a 56# % MN REPS |
|---|---|---|---|---|---|---|---|---|---|
| Hybrid 1 | 94 | 148 | | | 178.6 | 131 | 1 | 96.6 | 131 |
| Hybrid 2 | 93 | 213 | 94 | 191 | 184.8 | 107 | 3 | 101.2 | 107 |
| Hybrid 3 | 94 | 382 | 95 | 234 | 181.1 | 193 | 3 | 100.3 | 193 |
| Hybrid 4 | 94 | 22 | | | 179.2 | 5 | 1 | 97.4 | 5 |
| Hybrid 5 | 93 | 22 | | | 177.2 | 12 | 1 | 97.8 | 12 |
| Hybrid 6 | 99 | 232 | 100 | 232 | 185.6 | 171 | 3 | 100.5 | 171 |
| Hybrid 7 | | | | | 182.5 | 18 | 1 | 97.2 | 18 |
| Hybrid 8 | | | | | 185.1 | 18 | 1 | 98.2 | 18 |
| Hybrid 9 | | | | | 177.1 | 17 | 1 | 94.6 | 17 |
| Hybrid 10 | | | | | 170.8 | 18 | 1 | 91.4 | 18 |
| Hybrid 11 | | | | | 178.6 | 18 | 1 | 94.9 | 18 |
| Hybrid 12 | 97 | 52 | 97 | 52 | 178.2 | 23 | 1 | 100.8 | 23 |
| Hybrid 13 | 92 | 64 | 92 | 64 | 174.1 | 32 | 2 | 102.9 | 32 |
| Hybrid 14 | 94 | 129 | 95 | 129 | 190.6 | 60 | 2 | 103 | 60 |
| Hybrid 15 | 94 | 202 | 92 | 202 | 181.1 | 85 | 2 | 99.2 | 85 |
| Hybrid 16 | 95 | 202 | 94 | 202 | 184.1 | 89 | 2 | 100.9 | 89 |
| Hybrid 17 | 93 | 22 | 92 | 22 | 188.5 | 10 | 1 | 99.5 | 10 |
| Hybrid 18 | 96 | 26 | 95 | 26 | 171.7 | 15 | 1 | 96.6 | 15 |
| Hybrid 19 | 94 | 22 | 95 | 22 | 193.1 | 11 | 1 | 101.7 | 11 |
| Hybrid 20 | 94 | 49 | 95 | 49 | 176.3 | 19 | 1 | 100.5 | 19 |
| Hybrid 21 | 101 | 52 | 97 | 52 | 183.7 | 24 | 1 | 103.7 | 24 |
| Hybrid 22 | 98 | 52 | 93 | 52 | 180.6 | 24 | 1 | 100.9 | 24 |
| Hybrid 23 | 96 | 52 | 96 | 52 | 181.7 | 24 | 1 | 103.6 | 24 |
| Hybrid 24 | 97 | 52 | 91 | 52 | 178.9 | 25 | 1 | 101.3 | 25 |
| Hybrid 25 | 96 | 52 | 96 | 52 | 171.8 | 17 | 1 | 97.8 | 17 |
| Hybrid 26 | 95 | 52 | 97 | 52 | 148.6 | 17 | 1 | 88.3 | 17 |
| Hybrid 27 | 93 | 18 | 93 | 18 | 188.6 | 11 | 1 | 104 | 11 |
| Hybrid 28 | 90 | 18 | 89 | 18 | 163.6 | 10 | 1 | 90 | 10 |
| Hybrid 29 | 93 | 22 | 94 | 22 | 180 | 10 | 1 | 95.8 | 10 |
| Hybrid 30 | 96 | 22 | 92 | 22 | 193.7 | 10 | 1 | 102 | 10 |
| Hybrid 31 | 96 | 22 | 92 | 22 | 202.4 | 11 | 1 | 106.3 | 11 |
| Hybrid 32 | | | 97 | 18 | | | | | |
| Hybrid 33 | 97 | 18 | 90 | 18 | 145.4 | 6 | 1 | 87.8 | 6 |
| Hybrid 34 | 91 | 18 | 92 | 18 | 177.3 | 10 | 1 | 99.2 | 10 |
| Hybrid 35 | 95 | 18 | 88 | 18 | 168.8 | 7 | 1 | 91.8 | 7 |
| Hybrid 36 | | | 94 | 18 | | | | | |
| Hybrid 37 | 97 | 22 | 94 | 22 | 191 | 11 | 1 | 100.7 | 11 |
| Hybrid 38 | 93 | 22 | 94 | 22 | 189 | 11 | 1 | 99.2 | 11 |
| Hybrid 39 | 95 | 22 | 93 | 22 | 190.7 | 11 | 1 | 100.2 | 11 |
| Hybrid 40 | 92 | 22 | 92 | 22 | 184.9 | 8 | 1 | 96.8 | 8 |

TABLE 6-continued

PHENOTYPIC DATA FROM HYBRIDS PRODUCED WITH PHF1J.

| | | | | | | | | | |
|---|---|---|---|---|---|---|---|---|---|
| Hybrid 41 | 97 | 18 | 94 | 18 | 190.5 | 11 | 1 | 104.4 | 11 |
| Hybrid 42 | 98 | 18 | 94 | 18 | 192.8 | 11 | 1 | 105.8 | 11 |
| Hybrid 43 | 94 | 18 | 93 | 18 | 188.9 | 10 | 1 | 103.6 | 10 |
| Hybrid 44 | 96 | 22 | 96 | 22 | 188.2 | 11 | 1 | 99 | 11 |
| Hybrid 45 | 93 | 18 | 92 | 18 | 186.4 | 11 | 1 | 102.7 | 11 |
| Hybrid 46 | 95 | 18 | 94 | 18 | 197.9 | 11 | 1 | 108.5 | 11 |
| Hybrid 47 | 98 | 26 | 94 | 26 | 158.7 | 15 | 1 | 89.4 | 15 |
| Hybrid 48 | 95 | 22 | 93 | 22 | 192.6 | 11 | 1 | 101.4 | 11 |
| Hybrid 49 | 95 | 22 | 93 | 22 | 193.1 | 11 | 1 | 101.7 | 11 |
| Hybrid 50 | 92 | 18 | 92 | 18 | 169.8 | 11 | 1 | 93.2 | 11 |
| Hybrid 51 | 87 | 88 | 87 | 88 | 173 | 43 | 2 | 100.2 | 43 |
| Hybrid 52 | 91 | 229 | 91 | 229 | 181.1 | 116 | 3 | 102.1 | 116 |
| Hybrid 53 | 83 | 19 | 80 | 19 | 171.1 | 10 | 1 | 105.1 | 10 |
| Hybrid 54 | 90 | 168 | 89 | 168 | 181 | 86 | 2 | 101.4 | 86 |
| Hybrid 55 | 92 | 64 | 91 | 64 | 166.8 | 32 | 2 | 99 | 32 |
| Hybrid 56 | 92 | 64 | 92 | 64 | 177.3 | 33 | 2 | 104.5 | 33 |
| Hybrid 57 | 93 | 64 | 93 | 64 | 175.2 | 32 | 2 | 103.7 | 32 |
| Hybrid 58 | 97 | 64 | 92 | 64 | 177.4 | 33 | 2 | 104.8 | 33 |
| Hybrid 59 | 94 | 49 | 96 | 49 | 166.2 | 19 | 1 | 94.8 | 19 |
| Hybrid 60 | 94 | 64 | 92 | 64 | 185.1 | 16 | 2 | 103.5 | 16 |
| Hybrid 61 | 91 | 168 | 91 | 168 | 180.3 | 86 | 2 | 101.3 | 86 |
| Hybrid 62 | 96 | 22 | 97 | 22 | 198.1 | 11 | 1 | 104.2 | 11 |
| Hybrid 63 | 92 | 18 | 89 | 18 | 174.2 | 11 | 1 | 96.5 | 11 |
| Hybrid 64 | 89 | 64 | 94 | 64 | 170.9 | 24 | 2 | 99.5 | 24 |

| | MST pct ABS MEAN | MST pct ABS REPS | MST pct % MN MEAN | MST pct % MN REPS | YLD MST Value ABS MEAN | YLD MST Value ABS REPS | STL PCN % NOT % MN MEAN | STL PCN % NOT % MN REPS | STL LPN % NOT % MN MEAN |
|---|---|---|---|---|---|---|---|---|---|
| Hybrid 1 | 21.4 | 133 | 97.1 | 133 | 99.8 | 130 | 92 | 19 | 123 |
| Hybrid 2 | 24 | 107 | 96.4 | 107 | 105.1 | 112 | 101 | 12 | 98 |
| Hybrid 3 | 19.8 | 193 | 97.1 | 193 | 103.2 | 193 | 105 | 35 | 109 |
| Hybrid 4 | 19.2 | 5 | 99.1 | 5 | 98.3 | 5 | | | |
| Hybrid 5 | 18.9 | 12 | 96.8 | 12 | 100.9 | 12 | | | |
| Hybrid 6 | 23 | 171 | 97.8 | 171 | 102.7 | 171 | 104 | 29 | 109 |
| Hybrid 7 | 19.9 | 18 | 99.4 | 18 | 97.8 | 18 | | | |
| Hybrid 8 | 20 | 18 | 99.7 | 18 | 98.6 | 18 | | | |
| Hybrid 9 | 19.8 | 17 | 99 | 17 | 95.7 | 17 | | | |
| Hybrid 10 | 19.5 | 18 | 97.4 | 18 | 94 | 18 | | | |
| Hybrid 11 | 19 | 18 | 95.1 | 18 | 99.9 | 18 | | | |
| Hybrid 12 | 20.5 | 23 | 100.9 | 23 | 98.8 | 27 | 107 | 2 | 103 |
| Hybrid 13 | 26.6 | 32 | 100.8 | 32 | 103.3 | 32 | 87 | 6 | 104 |
| Hybrid 14 | 23.5 | 60 | 95 | 60 | 107.8 | 67 | 109 | 3 | 107 |
| Hybrid 15 | 21.4 | 85 | 99.7 | 85 | 99.3 | 89 | 105 | 10 | 106 |
| Hybrid 16 | 22.1 | 90 | 100.3 | 90 | 100.7 | 93 | 101 | 12 | 107 |
| Hybrid 17 | 22 | 10 | 97.7 | 10 | 101 | 11 | 96 | 2 | 92 |
| Hybrid 18 | 20.7 | 15 | 99.6 | 15 | 96 | 16 | 111 | 1 | 108 |
| Hybrid 19 | 22.2 | 11 | 100.5 | 11 | 100.3 | 12 | 106 | 2 | 103 |
| Hybrid 20 | 21.4 | 19 | 99.2 | 19 | 100.5 | 22 | 115 | 3 | 118 |
| Hybrid 21 | 21.4 | 24 | 107.9 | 24 | 95.9 | 29 | 108 | 2 | 107 |
| Hybrid 22 | 20.8 | 25 | 103.3 | 25 | 96.2 | 29 | 101 | 2 | 107 |
| Hybrid 23 | 20.2 | 24 | 101.3 | 24 | 103.5 | 28 | 109 | 2 | 118 |
| Hybrid 24 | 20.6 | 25 | 102 | 25 | 98.8 | 29 | 106 | 2 | 114 |
| Hybrid 25 | 19.8 | 18 | 103.4 | 18 | 92.8 | 21 | 107 | 2 | 121 |
| Hybrid 26 | 19.3 | 17 | 107.7 | 17 | 75.2 | 21 | 106 | 1 | 110 |
| Hybrid 27 | 26.5 | 11 | 98.6 | 11 | 103.6 | 12 | | | 107 |
| Hybrid 28 | 25.2 | 10 | 94.4 | 10 | 96.1 | 11 | | | |
| Hybrid 29 | 21.9 | 10 | 97.8 | 10 | 99.2 | 11 | 109 | 2 | 111 |
| Hybrid 30 | 23.2 | 10 | 102.7 | 10 | 99.9 | 11 | 97 | 2 | 106 |
| Hybrid 31 | 23.2 | 11 | 104.7 | 11 | 101.2 | 12 | 101 | 2 | 88 |
| Hybrid 32 | | | | | | | | | |
| Hybrid 33 | 30 | 6 | 105.1 | 6 | 84.4 | 7 | | | |
| Hybrid 34 | 25.6 | 10 | 95.7 | 10 | 103 | 11 | | | 102 |
| Hybrid 35 | 27.5 | 7 | 102.5 | 7 | 89.3 | 7 | | | |
| Hybrid 36 | | | | | | | | | |
| Hybrid 37 | 23.7 | 11 | 106.7 | 11 | 94.7 | 12 | 109 | 2 | 111 |
| Hybrid 38 | 22.2 | 11 | 100.1 | 11 | 99.3 | 12 | 110 | 2 | 112 |
| Hybrid 39 | 22.6 | 11 | 101.5 | 11 | 97.6 | 12 | 102 | 2 | 109 |
| Hybrid 40 | 21.7 | 8 | 99 | 8 | 98.5 | 9 | 108 | 1 | 100 |
| Hybrid 41 | 29 | 11 | 108.3 | 11 | 97.3 | 12 | | | 112 |
| Hybrid 42 | 29.1 | 11 | 108 | 11 | 96.5 | 12 | | | 103 |
| Hybrid 43 | 26.7 | 10 | 99.4 | 10 | 103.1 | 11 | | | |
| Hybrid 44 | 23.2 | 11 | 104.7 | 11 | 94.5 | 12 | 103 | 2 | 99 |
| Hybrid 45 | 26.7 | 11 | 99.3 | 11 | 104.1 | 12 | | | 112 |

TABLE 6-continued

PHENOTYPIC DATA FROM HYBRIDS PRODUCED WITH PHF1J.

| | | | | | | | | | |
|---|---|---|---|---|---|---|---|---|---|
| Hybrid 46 | 27.8 | 11 | 103.6 | 11 | 105 | 12 | | | 98 |
| Hybrid 47 | 21.4 | 15 | 102.5 | 15 | 86.9 | 16 | 111 | 1 | 106 |
| Hybrid 48 | 22.9 | 11 | 103.5 | 11 | 98 | 12 | 110 | 2 | 109 |
| Hybrid 49 | 22.9 | 11 | 103.5 | 11 | 97.6 | 12 | 108 | 2 | 96 |
| Hybrid 50 | 26.2 | 11 | 97.4 | 11 | 96.3 | 12 | | | 102 |
| Hybrid 51 | 24.9 | 43 | 96.5 | 43 | 103.5 | 43 | 96 | 9 | 102 |
| Hybrid 52 | 25 | 117 | 98.2 | 117 | 104.2 | 119 | 108 | 27 | 111 |
| Hybrid 53 | 25 | 10 | 95.1 | 10 | 106.8 | 10 | 112 | 1 | 121 |
| Hybrid 54 | 25.2 | 86 | 98.6 | 86 | 102.5 | 88 | 87 | 21 | 97 |
| Hybrid 55 | 26.8 | 32 | 101.5 | 32 | 97.4 | 33 | 110 | 6 | 108 |
| Hybrid 56 | 26.7 | 33 | 101.8 | 33 | 104.5 | 34 | 95 | 6 | 100 |
| Hybrid 57 | 27.3 | 32 | 103.7 | 32 | 100.7 | 32 | 116 | 6 | 105 |
| Hybrid 58 | 28.6 | 33 | 109 | 33 | 96.3 | 34 | 107 | 6 | 109 |
| Hybrid 59 | 21.6 | 19 | 99.9 | 19 | 95.2 | 23 | 115 | 3 | 80 |
| Hybrid 60 | 27.6 | 16 | 99.9 | 16 | 103.4 | 17 | 106 | 1 | 110 |
| Hybrid 61 | 25.1 | 87 | 99 | 87 | 102 | 88 | 99 | 21 | 96 |
| Hybrid 62 | 23.1 | 11 | 104.1 | 11 | 97.6 | 12 | 88 | 2 | 115 |
| Hybrid 63 | 26.2 | 11 | 97.3 | 11 | 100.1 | 12 | | | 98 |
| Hybrid 64 | 25.4 | 25 | 98.8 | 25 | 99.4 | 24 | 111 | 5 | 107 |

| | STL LPN % NOT % MN MEAN | ERT LPN % NOT % MN REPS | ERT LPN % NOT % MN MEAN | LRT LPN % NOT % MN REPS | LRT LPN % NOT % MN MEAN | TST WT lb/bu % MN MEAN | TST WT lb/bu % MN REPS | STK CNT count % MN MEAN | STK CNT count % MN REPS |
|---|---|---|---|---|---|---|---|---|---|
| Hybrid 1 | 5 | 89 | 7 | 102 | 17 | 101.2 | 88 | 101 | 193 |
| Hybrid 2 | 32 | 132 | 4 | 102 | 8 | 101.9 | 23 | 100 | 197 |
| Hybrid 3 | 33 | 97 | 20 | 96 | 27 | 102 | 167 | 101 | 343 |
| Hybrid 4 | | | | | | 102.1 | 5 | 101 | 7 |
| Hybrid 5 | | | | | | 102.1 | 12 | 101 | 15 |
| Hybrid 6 | 25 | 103 | 15 | 93 | 23 | 100.4 | 103 | 100 | 236 |
| Hybrid 7 | | | | 103 | 6 | 98.8 | 16 | 101 | 18 |
| Hybrid 8 | | | | 98 | 6 | 99 | 16 | 101 | 18 |
| Hybrid 9 | | | | 113 | 6 | 98.4 | 15 | 99 | 17 |
| Hybrid 10 | | | | 108 | 6 | 99.7 | 16 | 100 | 18 |
| Hybrid 11 | | | | 110 | 6 | 99.7 | 16 | 101 | 18 |
| Hybrid 12 | 2 | 108 | 1 | 84 | 6 | 100.2 | 14 | 100 | 48 |
| Hybrid 13 | 6 | 123 | 1 | 100 | 7 | 100.9 | 15 | 100 | 62 |
| Hybrid 14 | 13 | 109 | 4 | 108 | 4 | 100.4 | 15 | 99 | 113 |
| Hybrid 15 | 15 | 93 | 9 | 107 | 9 | 99.8 | 47 | 100 | 170 |
| Hybrid 16 | 18 | 95 | 11 | 101 | 10 | 99.9 | 47 | 99 | 181 |
| Hybrid 17 | 2 | 104 | 1 | 109 | 2 | 99.6 | 7 | 101 | 21 |
| Hybrid 18 | 3 | | | 66 | 2 | 98.9 | 12 | 100 | 26 |
| Hybrid 19 | 2 | 99 | 1 | 101 | 2 | 100.2 | 8 | 100 | 21 |
| Hybrid 20 | 3 | 113 | 1 | 84 | 5 | 101.4 | 11 | 101 | 41 |
| Hybrid 21 | 2 | 108 | 1 | 114 | 6 | 100.6 | 16 | 100 | 49 |
| Hybrid 22 | 2 | 100 | 1 | 105 | 6 | 101.2 | 16 | 100 | 50 |
| Hybrid 23 | 2 | 108 | 1 | 113 | 6 | 99.3 | 15 | 101 | 50 |
| Hybrid 24 | 2 | 108 | 1 | 100 | 6 | 101 | 16 | 100 | 50 |
| Hybrid 25 | 2 | | | 72 | 4 | 101.2 | 14 | 99 | 40 |
| Hybrid 26 | 2 | 102 | 1 | 120 | 4 | 100 | 14 | 99 | 38 |
| Hybrid 27 | 1 | | | 86 | 4 | 100.5 | 5 | 101 | 18 |
| Hybrid 28 | | | | 119 | 4 | 99.7 | 5 | 99 | 17 |
| Hybrid 29 | 2 | 104 | 1 | 107 | 2 | 99.2 | 7 | 100 | 20 |
| Hybrid 30 | 2 | 83 | 1 | 102 | 2 | 100.1 | 7 | 101 | 21 |
| Hybrid 31 | 2 | 104 | 1 | 85 | 2 | 98.1 | 8 | 101 | 21 |
| Hybrid 32 | | | | | | | | | |
| Hybrid 33 | | | | 115 | 2 | 98.4 | 2 | 101 | 10 |
| Hybrid 34 | 1 | | | 107 | 4 | 100.7 | 4 | 100 | 16 |
| Hybrid 35 | | | | 100 | 3 | 98.4 | 3 | 97 | 9 |
| Hybrid 36 | | | | | | | | 92 | 1 |
| Hybrid 37 | 2 | 100 | 1 | 77 | 2 | 99.9 | 8 | 101 | 21 |
| Hybrid 38 | 2 | 104 | 1 | 96 | 2 | 101.6 | 8 | 101 | 21 |
| Hybrid 39 | 2 | 104 | 1 | 100 | 2 | 102.1 | 8 | 100 | 21 |
| Hybrid 40 | 2 | 101 | 1 | 97 | 1 | 100.7 | 6 | 100 | 16 |
| Hybrid 41 | 1 | | | 89 | 4 | 97.8 | 5 | 100 | 17 |
| Hybrid 42 | 1 | | | 88 | 4 | 100.2 | 5 | 100 | 18 |
| Hybrid 43 | | | | 101 | 4 | 97.7 | 4 | 100 | 14 |
| Hybrid 44 | 2 | 99 | 1 | 89 | 2 | 101.6 | 8 | 100 | 21 |
| Hybrid 45 | 1 | | | 85 | 4 | 98.4 | 5 | 101 | 18 |
| Hybrid 46 | 1 | | | 114 | 4 | 99.1 | 5 | 100 | 18 |
| Hybrid 47 | 2 | | | 154 | 2 | 100.8 | 11 | 101 | 24 |
| Hybrid 48 | 2 | 104 | 1 | 107 | 2 | 99.1 | 8 | 100 | 21 |
| Hybrid 49 | 2 | 104 | 1 | 74 | 2 | 99.1 | 8 | 101 | 21 |
| Hybrid 50 | 1 | | | 117 | 4 | 100.8 | 5 | 101 | 18 |

TABLE 6-continued

PHENOTYPIC DATA FROM HYBRIDS PRODUCED WITH PHF1J.

| | | | | | | | | | |
|---|---|---|---|---|---|---|---|---|---|
| Hybrid 51 | 12 | | | 120 | 9 | 101 | 18 | 100 | 77 |
| Hybrid 52 | 22 | 96 | 8 | 114 | 13 | 99.8 | 49 | 100 | 214 |
| Hybrid 53 | 1 | | | 74 | 2 | 101.9 | 4 | 99 | 16 |
| Hybrid 54 | 17 | 75 | 5 | 103 | 10 | 102.2 | 37 | 100 | 171 |
| Hybrid 55 | 6 | | | 95 | 7 | 100.8 | 15 | 100 | 61 |
| Hybrid 56 | 4 | 116 | 1 | 87 | 7 | 100.4 | 16 | 100 | 61 |
| Hybrid 57 | 6 | 128 | 1 | 92 | 7 | 100.1 | 15 | 100 | 61 |
| Hybrid 58 | 6 | 94 | 1 | 87 | 7 | 98 | 16 | 101 | 62 |
| Hybrid 59 | 3 | 84 | 1 | 97 | 5 | 102.3 | 11 | 99 | 44 |
| Hybrid 60 | 2 | | | 65 | 3 | 99.4 | 6 | 100 | 26 |
| Hybrid 61 | 15 | 101 | 6 | 98 | 11 | 101.4 | 38 | 100 | 171 |
| Hybrid 62 | 2 | 91 | 1 | 106 | 2 | 98.7 | 8 | 101 | 20 |
| Hybrid 63 | 1 | | | 120 | 4 | 100.6 | 5 | 101 | 18 |
| Hybrid 64 | 4 | 121 | 1 | 98 | 5 | 102.6 | 14 | 101 | 47 |

| | PLTHT in % MN MEAN | PLTHT in % MN REPS | EAR HT in % MN MEAN | EAR HT in % MN REPS | BRT STK % NOT % MN MEAN | BRT STK % NOT % MN REPS | BOR BMN % NOT % MN MEAN | BOR BMN % NOT % MN REPS | BREN GMN kg*mm % MN MEAN |
|---|---|---|---|---|---|---|---|---|---|
| Hybrid 1 | 98 | 48 | 103 | 48 | 99 | 4 | | | |
| Hybrid 2 | 100 | 49 | 102 | 49 | 100 | 2 | | | 95 |
| Hybrid 3 | 99 | 67 | 100 | 67 | 100 | 8 | 103 | 8 | 99.3 |
| Hybrid 4 | 98 | 3 | 106 | 3 | | | | | |
| Hybrid 5 | 98 | 7 | 103 | 7 | | | | | |
| Hybrid 6 | 99 | 46 | 107 | 46 | 104 | 4 | | | 94.1 |
| Hybrid 7 | 103 | 6 | 106 | 6 | | | | | |
| Hybrid 8 | 99 | 6 | 104 | 6 | | | | | |
| Hybrid 9 | 101 | 6 | 106 | 6 | | | | | |
| Hybrid 10 | 99 | 6 | 107 | 6 | | | | | |
| Hybrid 11 | 101 | 6 | 101 | 6 | | | | | |
| Hybrid 12 | 100 | 9 | 100 | 9 | | | 101 | 2 | |
| Hybrid 13 | 100 | 15 | 105 | 15 | | | 112 | 4 | 98.8 |
| Hybrid 14 | 103 | 27 | 109 | 27 | 101 | 2 | | | |
| Hybrid 15 | 99 | 37 | 105 | 37 | 101 | 2 | 98 | 4 | |
| Hybrid 16 | 102 | 37 | 104 | 37 | 101 | 3 | 102 | 4 | 101.2 |
| Hybrid 17 | 100 | 6 | 101 | 6 | | | | | |
| Hybrid 18 | 98 | 10 | 101 | 10 | | | | | |
| Hybrid 19 | 100 | 6 | 102 | 6 | | | | | |
| Hybrid 20 | 98 | 7 | 99 | 7 | | | 103 | 4 | |
| Hybrid 21 | 98 | 10 | 97 | 10 | | | 95 | 2 | |
| Hybrid 22 | 96 | 10 | 99 | 10 | | | 103 | 2 | |
| Hybrid 23 | 99 | 10 | 105 | 10 | | | 99 | 2 | |
| Hybrid 24 | 101 | 10 | 103 | 10 | | | 99 | 2 | |
| Hybrid 25 | 104 | 10 | 107 | 10 | | | 103 | 2 | |
| Hybrid 26 | 102 | 9 | 99 | 9 | | | 101 | 2 | |
| Hybrid 27 | 105 | 6 | 111 | 6 | | | | | |
| Hybrid 28 | 98 | 6 | 94 | 6 | | | | | |
| Hybrid 29 | 98 | 5 | 97 | 5 | | | | | |
| Hybrid 30 | 103 | 6 | 101 | 6 | | | | | |
| Hybrid 31 | 100 | 6 | 103 | 6 | | | | | |
| Hybrid 32 | | | | | | | | | |
| Hybrid 33 | 98 | 3 | 95 | 3 | | | | | |
| Hybrid 34 | 99 | 5 | 102 | 5 | | | | | |
| Hybrid 35 | 97 | 5 | 96 | 5 | | | | | |
| Hybrid 36 | 99 | 1 | 100 | 1 | | | | | |
| Hybrid 37 | 101 | 6 | 100 | 6 | | | | | |
| Hybrid 38 | 100 | 6 | 102 | 6 | | | | | |
| Hybrid 39 | 99 | 6 | 102 | 6 | | | | | |
| Hybrid 40 | 99 | 5 | 100 | 5 | | | | | |
| Hybrid 41 | 100 | 6 | 102 | 6 | | | | | |
| Hybrid 42 | 103 | 6 | 107 | 6 | | | | | |
| Hybrid 43 | 101 | 5 | 103 | 5 | | | | | |
| Hybrid 44 | 100 | 6 | 103 | 6 | | | | | |
| Hybrid 45 | 102 | 6 | 106 | 6 | | | | | |
| Hybrid 46 | 100 | 6 | 104 | 6 | | | | | |
| Hybrid 47 | 99 | 9 | 99 | 9 | | | | | |
| Hybrid 48 | 97 | 6 | 97 | 6 | | | | | |
| Hybrid 49 | 101 | 6 | 102 | 6 | | | | | |
| Hybrid 50 | 102 | 6 | 102 | 6 | | | | | |
| Hybrid 51 | 96 | 16 | 99 | 16 | | | 80 | 4 | 102.9 |
| Hybrid 52 | 99 | 45 | 100 | 45 | 107 | 2 | 102 | 12 | 93.7 |
| Hybrid 53 | 101 | 5 | 105 | 5 | | | | | |
| Hybrid 54 | 100 | 28 | 102 | 28 | 99 | 1 | 104 | 12 | 94.8 |
| Hybrid 55 | 98 | 15 | 103 | 15 | | | 108 | 4 | |

TABLE 6-continued

PHENOTYPIC DATA FROM HYBRIDS PRODUCED WITH PHF1J.

| | | | | | | | | |
|---|---|---|---|---|---|---|---|---|
| Hybrid 56 | 101 | 15 | 104 | 15 | | | 111 | 4 |
| Hybrid 57 | 101 | 15 | 103 | 15 | | | 103 | 4 |
| Hybrid 58 | 101 | 15 | 103 | 15 | | | 110 | 4 |
| Hybrid 59 | 101 | 8 | 99 | 8 | | | 95 | 4 |
| Hybrid 60 | 103 | 9 | 105 | 9 | | | | |
| Hybrid 61 | 98 | 30 | 104 | 30 | 101 | 1 | 109 | 12 | 95.8 |
| Hybrid 62 | 104 | 6 | 111 | 6 | | | | |
| Hybrid 63 | 98 | 6 | 96 | 6 | | | | |
| Hybrid 64 | 98 | 10 | 100 | 11 | | | 96 | 4 |

| | BREN GMN kg*mm % MN REPS | GLF SPT score ABS MEAN | GLF SPT score ABS REPS | STA GRN score ABS MEAN | STA GRN score ABS REPS | HSK CVR score ABS MEAN | HSK CVR score ABS REPS | ECB LSI score ABS MEAN | ECB LSI score ABS REPS |
|---|---|---|---|---|---|---|---|---|---|
| Hybrid 1 | | 5 | 4 | 5 | 42 | 7 | 19 | 4.5 | 4 |
| Hybrid 2 | 4 | 7 | 2 | 6 | 33 | 7 | 18 | 5.7 | 7 |
| Hybrid 3 | 10 | 5 | 10 | 6 | 62 | 6 | 26 | | |
| Hybrid 4 | | | | 6 | 2 | | | | |
| Hybrid 5 | | | | 7 | 5 | | | | |
| Hybrid 6 | 7 | 6 | 3 | 5 | 37 | 5 | 9 | 3 | 1 |
| Hybrid 7 | | | | 5 | 2 | | | | |
| Hybrid 8 | | | | 6 | 2 | | | | |
| Hybrid 9 | | | | 6 | 2 | | | | |
| Hybrid 10 | | | | 5 | 2 | | | | |
| Hybrid 11 | | | | 5 | 2 | | | | |
| Hybrid 12 | | 4 | 2 | 6 | 2 | | | | |
| Hybrid 13 | | | | 3 | 6 | 5 | 3 | 7 | 3 |
| Hybrid 14 | 4 | 5 | 6 | 7 | 16 | 5 | 15 | 4.4 | 8 |
| Hybrid 15 | | 5 | 4 | 6 | 23 | 5 | 16 | 5.6 | 7 |
| Hybrid 16 | 4 | 4 | 4 | 5 | 24 | 6 | 17 | 5.6 | 7 |
| Hybrid 17 | | | | 4 | 2 | | | | |
| Hybrid 18 | | | | 6 | 1 | | | | |
| Hybrid 19 | | | | 5 | 2 | | | | |
| Hybrid 20 | | | | | | 5 | 1 | | |
| Hybrid 21 | | 5 | 2 | 6 | 2 | | | | |
| Hybrid 22 | | 5 | 2 | 7 | 2 | | | | |
| Hybrid 23 | | 5 | 2 | 7 | 2 | | | | |
| Hybrid 24 | | 4 | 2 | 7 | 2 | | | | |
| Hybrid 25 | | 5 | 2 | 7 | 1 | | | | |
| Hybrid 26 | | 4 | 2 | 7 | 2 | | | | |
| Hybrid 27 | | | | 4 | 2 | | | | |
| Hybrid 28 | | | | 4 | 2 | | | | |
| Hybrid 29 | | | | 6 | 1 | | | | |
| Hybrid 30 | | | | 4 | 2 | | | | |
| Hybrid 31 | | | | 4 | 2 | | | | |
| Hybrid 32 | | | | | | | | | |
| Hybrid 33 | | | | 4 | 2 | | | | |
| Hybrid 34 | | | | 3 | 2 | | | | |
| Hybrid 35 | | | | 5 | 2 | | | | |
| Hybrid 36 | | | | | | | | | |
| Hybrid 37 | | | | 6 | 1 | | | | |
| Hybrid 38 | | | | 6 | 2 | | | | |
| Hybrid 39 | | | | 7 | 2 | | | | |
| Hybrid 40 | | | | 5 | 1 | | | | |
| Hybrid 41 | | | | 5 | 2 | | | | |
| Hybrid 42 | | | | 4 | 2 | | | | |
| Hybrid 43 | | | | 3 | 2 | | | | |
| Hybrid 44 | | | | 6 | 2 | | | | |
| Hybrid 45 | | | | 5 | 2 | | | | |
| Hybrid 46 | | | | 5 | 2 | | | | |
| Hybrid 47 | | | | | | | | | |
| Hybrid 48 | | | | 6 | 2 | | | | |
| Hybrid 49 | | | | 4 | 2 | | | | |
| Hybrid 50 | | | | 3 | 2 | | | | |
| Hybrid 51 | 4 | | | 3 | 6 | 6 | 7 | 6 | 2 |
| Hybrid 52 | 8 | 5 | 2 | 6 | 28 | 5 | 26 | 5.3 | 6 |
| Hybrid 53 | | | | 4 | 2 | 5 | 1 | | |
| Hybrid 54 | 4 | 5 | 2 | 3 | 24 | 6 | 24 | 6 | 6 |
| Hybrid 55 | | | | 4 | 6 | 5 | 4 | 7 | 2 |
| Hybrid 56 | | | | 4 | 5 | 5 | 4 | 5.3 | 3 |
| Hybrid 57 | | | | 5 | 6 | 5 | 3 | 6 | 2 |
| Hybrid 58 | | | | 5 | 6 | 5 | 4 | 5 | 1 |
| Hybrid 59 | | | | | | 7 | 1 | | |
| Hybrid 60 | | | | 5 | 2 | 7 | 2 | | |

TABLE 6-continued

PHENOTYPIC DATA FROM HYBRIDS PRODUCED WITH PHF1J.

| Hybrid 61 | 4 | 5 | 2 | 4 | 23 | 6 | 24 | 5.8 | 6 |
|---|---|---|---|---|---|---|---|---|---|
| Hybrid 62 | | | | 5 | 2 | | | | |
| Hybrid 63 | | | | 3 | 2 | | | | |
| Hybrid 64 | | | | 6 | 4 | 6 | 3 | 6 | 1 |

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A seed comprising at least one set of the chromosomes of maize inbred line PHF1J, representative seed of said line having been deposited under ATCC Accession Number PTA-7773, wherein said chromosomes comprise all of the alleles of inbred line PHF1J at the SSR loci listed in Table 2.

2. A maize seed produced by crossing a plant produced by growing the seed of claim 1 with a different maize plant.

3. A maize plant produced by growing the maize seed of claim 2.

4. A plant part of the maize plant of claim 3.

5. A method for developing maize seed comprising crossing the plant of claim 3 with a different maize plant.

6. A method for developing a second maize plant in a maize plant breeding program comprising applying plant breeding techniques to a first maize plant, or parts thereof, wherein said first maize plant is the maize plant of claim 3, and wherein application of said techniques results in development of said second maize plant.

\* \* \* \* \*